(12) United States Patent
Spodsberg et al.

(10) Patent No.: US 9,068,176 B2
(45) Date of Patent: Jun. 30, 2015

(54) POLYPEPTIDES HAVING ENDOGLUCANASE ACTIVITY AND POLYNUCLEOTIDES ENCODING SAME

(75) Inventors: Nikolaj Spodsberg, Bagsvaerd (DK); Tarana Shagasi, Dixon, CA (US)

(73) Assignees: Novozymes A/S, Bagsvaerd (DK); Novozymes, Inc., Davis, CA (US)

(*) Notice: Subject to any disclaimer, the term of this patent is extended or adjusted under 35 U.S.C. 154(b) by 80 days.

(21) Appl. No.: 13/997,715

(22) PCT Filed: Jan. 26, 2012

(86) PCT No.: PCT/US2012/022704
§ 371 (c)(1),
(2), (4) Date: Jun. 25, 2013

(87) PCT Pub. No.: WO2012/103322
PCT Pub. Date: Aug. 2, 2012

(65) Prior Publication Data
US 2013/0288301 A1    Oct. 31, 2013

Related U.S. Application Data

(60) Provisional application No. 61/576,518, filed on Dec. 16, 2011.

(30) Foreign Application Priority Data

Jan. 26, 2011 (EP) .................................. 11152252

(51) Int. Cl.
| | |
|---|---|
| C12P 21/06 | (2006.01) |
| C12N 9/42 | (2006.01) |
| C12P 19/34 | (2006.01) |
| C12N 1/20 | (2006.01) |
| C12N 1/00 | (2006.01) |
| C12N 15/00 | (2006.01) |
| C12P 19/14 | (2006.01) |
| C07H 21/04 | (2006.01) |
| C07K 1/00 | (2006.01) |
| C12P 21/00 | (2006.01) |

(52) U.S. Cl.
CPC ....... *C12N 9/2437* (2013.01); *C12Y 302/01091* (2013.01); *C12P 19/14* (2013.01); *C12P 21/00* (2013.01)

(58) Field of Classification Search
CPC . C12Y 302/01091; C12P 21/00; C12P 19/14; C12N 9/2437

USPC ............ 435/69.1, 209, 91.1, 252.3, 254.11, 435/320.1, 99; 536/23.1, 23.2; 530/350
See application file for complete search history.

(56) References Cited

U.S. PATENT DOCUMENTS

| RE32,153 E | 5/1986 | Tamura et al. |
|---|---|---|
| 4,894,338 A | 1/1990 | Knowles et al. |
| 2011/0111453 A1 | 5/2011 | McBrayer et al. |

FOREIGN PATENT DOCUMENTS

| WO | 01/70998 A1 | 9/2001 |
|---|---|---|
| WO | 2007/115201 A2 | 10/2007 |
| WO | 2011/000949 A1 | 1/2011 |
| WO | 2011/153516 A2 | 12/2011 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Birren et al., UniProt Accession No. Q0CC79 (2006).
Federova et al., UniProt Accession No. A1DKY9 (2007).
Wei et al., Journal of Microbiology and Biotechnology, vol. 20, No. 2, pp. 265-270 (2010).

* cited by examiner

*Primary Examiner* — Ganapathirama Raghu
(74) *Attorney, Agent, or Firm* — Eric J. Fechter

(57) ABSTRACT

The present invention relates to isolated polypeptides having endoglucanase activity, catalytic domains, cellulose binding domains and polynucleotides encoding the polypeptides, catalytic domains or cellulose binding domains. The invention also relates to nucleic acid constructs, vectors, and host cells comprising the polynucleotides as well as methods of producing and using the polypeptides, catalytic domains or cellulose binding domains.

29 Claims, No Drawings

POLYPEPTIDES HAVING ENDOGLUCANASE ACTIVITY AND POLYNUCLEOTIDES ENCODING SAME

CROSS-REFERENCE TO RELATED APPLICATIONS

This application is a 35 U.S.C. 371 national application of PCT/US2012/022704 filed Jan. 26, 2012, which claims priority or the benefit under 35 U.S.C. 119 of European application no. 11152252.0 filed Jan. 26, 2011 and U.S. provisional application no. 61/576,518 filed Dec. 16, 2011, the contents of which are fully incorporated herein by reference.

STATEMENT AS TO RIGHTS TO INVENTIONS MADE UNDER FEDERALLY SPONSORED RESEARCH AND DEVELOPMENT

This invention was made with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form, which is incorporated herein by reference.

BACKGROUND OF THE INVENTION

1. Field of the Invention

The present invention relates to polypeptides having endoglucanase activity, catalytic domains, and cellulose binding domains, and polynucleotides encoding the polypeptides, catalytic domains, and cellulose binding domains. The present invention also relates to nucleic acid constructs, vectors, and host cells comprising the polynucleotides as well as methods of producing and using the polypeptides, catalytic domains, and cellulose binding domains.

2. Description of the Related Art

Cellulose is a polymer of the simple sugar glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the lignocellulose is converted to fermentable sugars, e.g., glucose, the fermentable sugars are easily fermented by yeast into ethanol.

The present invention provides polypeptides having endoglucanase activity and polynucleotides encoding the polypeptides. The deduced amino acid sequence of the *Talaromyces leycettanus* gene encoding the P23YSZ GH7 polypeptide having endoglucanase activity shares 74.2% identity (excluding gaps) to the deduced amino acid sequence of a predicted GH7 family protein from *Neosartorya fischeri* (accession number SWISSPROT:A1DKY9) with endoglucanase activity.

SUMMARY OF THE INVENTION

The present invention relates to isolated polypeptides having endoglucanase activity, selected from the group consisting of:

(a) a polypeptide having at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;

(b) a polypeptide encoded by a polynucleotide that hybridizes under medium-high stringency conditions, high stringency conditions, or very high stringency conditions with (i) the mature polypeptide coding sequence of SEQ ID NO: 1, or (ii) the full-length complement of (i);

(c) a polypeptide encoded by a polynucleotide having at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;

(d) a variant of the mature polypeptide of SEQ ID NO: 2 comprising a substitution, deletion, and/or insertion at one or several positions; and (e) a fragment of the polypeptide of (a), (b), (c), or (d) that has endoglucanase activity.

The present invention also relates to isolated polypeptide comprising a catalytic domain selected from the group consisting of:

(a) a catalytic domain having at least 80% sequence identity to amino acids 19 to 397 of SEQ ID NO: 2;

(b) a catalytic domain encoded by a polynucleotide that hybridizes under high, or very high stringency conditions with (i) nucleotides 55 to 1191 of SEQ ID NO: 1, or (ii) the full-length complement of (i);

(c) a catalytic domain encoded by a polynucleotide having at least 80% sequence identity to the catalytic domain of SEQ ID NO: 1;

(d) a variant of amino acids 19 to 397 of SEQ ID NO: 2 comprising a substitution, deletion, and/or insertion at one or several positions; and (e) a fragment of the catalytic domain of (a), (b), (c), or (d) that has endoglucanase activity.

The present invention also relates to an isolated polypeptide comprising a cellulose binding domain operably linked to a catalytic domain, wherein the binding domain is selected from the roup consisting of:

(a) a cellulose binding domain having at least 80% sequence identity to amino acids 444 to 477 of SEQ ID NO: 2;

(b) a cellulose binding domain encoded by a polynucleotide that hybridizes under high, or very high stringency conditions with (i) nucleotides 1333 to 1431 of SEQ ID NO: 1, or (ii) the full-length complement of (i);

(c) a cellulose binding domain encoded by a polynucleotide having at least 80% sequence identity to nucleotides 1333 to 1431 of SEQ ID NO: 1;

(d) a variant of amino acids 444 to 477 of SEQ ID NO: 2 comprising a substitution, deletion, and/or insertion at one or several positions; and (e) a fragment of (a), (b), (c), (d) or (e) that has cellulose binding activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to methods for degrading or converting a cellulosic material, comprising: treating the cellulosic material with an enzyme composition in the presence of a polypeptide having endoglucanase activity of the present invention. In one aspect, the method further comprises recovering the degraded or converted cellulosic material.

The present invention also relates to methods of producing a fermentation product, comprising: (a) saccharifying a cellulosic material with an enzyme composition in the presence of a polypeptide having endoglucanase activity of the present invention; (b) fermenting the saccharified cellulosic material with one or more (e.g., several) fermenting microorganisms to produce the fermentation product; and (c) recovering the fermentation product from the fermentation.

The present invention also relates to methods of fermenting a cellulosic material, comprising: fermenting the cellulosic material with one or more (e.g., several) fermenting microorganisms, wherein the cellulosic material is saccharified with an enzyme composition in the presence of a polypeptide having endoglucanase activity of the present invention. In one aspect, the fermenting of the cellulosic material produces a fermentation product. In another aspect, the method further comprises recovering the fermentation product from the fermentation.

The present invention also relates to a polynucleotide encoding a signal peptide comprising or consisting of amino acids 1 to 18 of SEQ ID NO: 2, which is operably linked to a gene encoding a protein, wherein the gene is foreign to the polynucleotide encoding the signal peptide; nucleic acid constructs, expression vectors, and recombinant host cells comprising the polynucleotide; and methods of producing a protein.

DEFINITIONS

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Binding domain: The term "cellulose binding domain" means the region of an enzyme that mediates binding of the enzyme to amorphous regions of a cellulose substrate. The cellulose binding domain (CBD) is typically found either at the N-terminal or at the C-terminal extremity of an endoglucanase. In one embodiment the CBD comprises amino acids 444 to 477 of SEQ ID NO: 2.

Catalytic domain: The term "catalytic domain" means the region of an enzyme containing the catalytic machinery of the enzyme. In one embodiment the catalytic domain comprises amino acids 19 to 397 of SEQ ID NO: 2.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic domain having one or more (e.g., several) amino acids absent from the amino and/or carboxyl terminus of a mature polypeptide or catalytic domain; wherein the fragment has endoglucanase activity. In one aspect, a fragment contains at least 379 amino acid residues (e.g., amino acids 19 to 397 of SEQ ID NO: 2).

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 19 to 477 of SEQ ID NO: 2 based on the SignalP (Nielsen et al., 1997, *Protein Engineering* 10: 1-6) that predicts amino acids 1 to 18 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having endoglucanase activity. In one aspect, the mature polypeptide coding sequence (including the stop codon) is nucleotides 55 to 1434 of SEQ ID NO: 1 based on the SignalP (Nielsen et al., 1997, supra) that predicts nucleotides 1 to 54 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having endoglucanase activity. In one aspect, a subsequence contains at least 1377 nucleotides (e.g., nucleotides 55 to 1431 of SEQ ID NO: 1).

Variant: The term "variant" means a polypeptide having endoglucanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Cellulolytic activity: The term "cellulolytic activity" means a biological activity that hydrolyzes a cellulosic material. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., 2006, Outlook for cellulase improvement: Screening and selection strategies, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic activity is determined by measuring the increase in hydrolysis of a cellulosic material by cellulolytic enzyme(s) under the following conditions: 1-20 mg of cellulolytic protein/g of cellulose in PCS for 3-7 days at 50-65° C. compared to a control hydrolysis without addition of cellulolytic protein. Typical conditions are 1 ml reactions, washed or unwashed PCS, 5% insoluble solids, 50 mM sodium acetate pH 5, 1 mM $MnSO_4$, 50-65° C., 72 hours, sugar analysis by AMINEX® HPX-87H column (Bio-Rad Laboratories, Inc., Hercules, Calif., USA).

Endoglucanase: The term "endoglucanase" means an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C. The assay described in Example 8 can be used to measure endoglucanase activity.

The polypeptides of the present invention have at least 20%, e.g., at least 40%, at least 50%, at least 60%, at least 70%, at least 80%, at least 90%, at least 95%, and at least 100% of the endoglucanase activity of the mature polypeptide of SEQ ID NO: 2.

Cellobiohydrolase: The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose 5 degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined using a fluorescent disaccharide derivative 4-methylumbelliferyl-β-D-lactoside according to the procedures described by van Tilbeurgh et al., 101982, *FEBS Letters* 149: 152-156 and van Tilbeurgh and Claeyssens, 1985, *FEBS Letters* 187: 283-288, at pH 5, 40° C.

Beta-glucosidase: The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 pmole of p-nitrophenol produced per minute at 40° C., pH 5 from 1 mM p-nitrophenyl-beta-D-glucopyranoside as substrate in 100 mM sodium citrate containing 0.01% TWEEN® 20.

Cellulolytic enhancing activity: The term "cellulolytic enhancing activity" means a biological activity catalyzed by a GH61 polypeptide that enhances the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic protein and 0.5-50% w/w protein of a GH61 polypeptide having cellulolytic enhancing activity for 1-7 day at 50-65° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5L (Novozymes A/S, Bagsvrd, Denmark) in the presence of 3% of total protein weight *Aspergillus oryzae* beta-glucosidase (recombinantly produced in *Aspergillus oryzae* according to WO 02/095014) or 3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-Fold, more preferably at least 4-fold, more preferably at least 5-fold, even more preferably at least 10-fold, and most preferably at least 20-fold.

Family 61 glycoside hydrolase: The term "Family 61 glycoside hydrolase" or "Family GH61" or "GH61" means a polypeptide falling into the glycoside hydrolase Family 61 according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Xylan degrading activity: The terms "xylan degrading activity" or "xylanolytic activity" mean a biological activity that hydrolyzes xylan-containing material. The two basic approaches for measuring xylanolytic activity include: (1) measuring the total xylanolytic activity, and (2) measuring the individual xylanolytic activities (endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann et al., 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endo-hydrolysis of 1,4-beta-D-xylosidic linkages in xylans. For purposes of the present invention, xylanase activity is determined using birchwood xylan as substrate. One unit of xylanase is defined as 1.0 μmole of reducing sugar (measured in glucose equivalents as described by Lever, 1972, A new reaction for colorimetric determination of carbohydrates, *Anal. Biochem* 47: 273-279) produced per minute during the initial period of hydrolysis at 50° C., pH 5 from 2 g of birchwood xylan per liter as substrate in 50 mM sodium acetate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase is defined as 1.0 μmole of p-nitrophenol produced per minute at 40° C., pH 5 from 1 mM p-nitrophenyl-beta-D-xyloside as substrate in 100 mM sodium citrate containing 0.01% TWEEN® 20.

Acetylxylan esterase: The term "acetylxylan esterase" means a carboxylesterase (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase is defined as the amount of enzyme capable of releasing 1 μmole of p-nitrophenolate anion per minute at pH 5, 25° C.

Feruloyl esterase: The term "feruloyl esterase" means a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 μmole of glucuronic or 4-O-methyl-glucuronic acid per minute at pH 5, 40° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Cellulosic material: The cellulosic material can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, N.Y.). It is understood herein that the cellulose may be in the form of lignocellulose, a plant cell wall material containing lignin, cellulose, and hemicellulose in a mixed matrix. In a preferred aspect, the cellulosic material is lignocellulose.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated corn stover: The term "PCS" or "Pretreated Corn Stover" means a cellulosic material derived from corn stover by treatment with heat and dilute sulfuric acid.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the methods of the present invention, any material containing xylan may be used. In a preferred aspect, the xylan-containing material is lignocellulose.

DETAILED DESCRIPTION OF THE INVENTION

Polypeptides Having Endoglucanase Activity

In an embodiment, the present invention relates to isolated polypeptides having a sequence identity to the mature polypeptide of SEQ ID NO: 2 of at least 75%, at least 80%, at least 85%, at least 90%, at least 91%, at least 92%, at least 93%, at least 94%, at least 95%, at least 96%, at least 97%, at least 98%, at least 99%, or 100%, which have endoglucanase activity. In one aspect, the polypeptides differ by no more than 10 amino acids, e.g., 1, 2, 3, 4, 5, 6, 7, 8, or 9, from the mature polypeptide of SEQ ID NO: 2.

The polypeptides of the present invention have at least 20%, e.g., at least 40%, at least 50%, at least 60%, at least 70%, at least 80%, at least 90%, at least 95%, and at least 100% of the endoglucanase activity of the mature polypeptide of SEQ ID NO: 2.

A polypeptide of the present invention preferably comprises or consists of the amino acid sequence of SEQ ID NO: 2 or an allelic variant thereof; or is a fragment thereof having endoglucanase activity. In another aspect, the polypeptide comprises or consists of the mature polypeptide of SEQ ID NO: 2. In another aspect, the polypeptide comprises or consists of amino acids 19 to 477 of SEQ ID NO: 2.

In another embodiment, the present invention relates to an isolated polypeptide having endoglucanase activity encoded by a polynucleotide that hybridizes under medium-high stringency conditions, high stringency conditions, or very high stringency conditions with (i) the mature polypeptide coding sequence of SEQ ID NO: 1, or (ii) the full-length complement of (i) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding polypeptides having endoglucanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having endoglucanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is nucleotides 1 to 1434, nucleotides 55 to 1434, or nucleotides 55 to 1191 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the present invention relates to an isolated polypeptide having endoglucanase activity encoded by a polynucleotide having a sequence identity to the mature polypeptide coding sequence of SEQ ID NO: 1 at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for endoglucanase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having Endoglucanase Activity

A polypeptide having endoglucanase activity of the present invention may be obtained from a fungus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a filamentous fungal polypeptide such as a Talaromyces polypeptide.

In another aspect, the polypeptide is a Talaromyces polypeptide, e.g., a polypeptide obtained from Talaromyces leycettanus. E.g. obtained from strain CBS398.68.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 19 to 397 of SEQ ID NO: 2 of at least 75%, at least 80%, at least 85%, at least 90%, at least 95%, at least 96%, at least 97%, at least 98%, at least 99%, or 100%. In one aspect, the catalytic domains comprise amino acid sequences that differ by no more than 10 amino acids, e.g., 1, 2, 3, 4, 5, 6, 7, 8, or 9, from amino acids 19 to 397 of SEQ ID NO: 2.

The catalytic domain preferably comprises or consists of amino acids 19 to 397 of SEQ ID NO: 2 or an allelic variant thereof; or is a fragment thereof having endoglucanase activity.

In another embodiment, the present invention also relates to catalytic domains encoded by polynucleotides that hybridize under high stringency conditions, or very high stringency conditions (as defined above) with (i) the nucleotides 55 to 1191 of SEQ ID NO: 1, or (ii) the full-length complement of (i) (Sambrook et al., 1989, supra).

In another embodiment, the present invention also relates to catalytic domains encoded by polynucleotides having a sequence identity to nucleotides 55 to 1191 of SEQ ID NO: 1 at least 75%, at least 80%, at least 85%, at least 90%, at least 95%, at least 96%, at least 97%, at least 98%, at least 99%, or 100%.

The polynucleotide encoding the catalytic domain preferably comprises or consists of nucleotides 55 to 1191 of SEQ ID NO: 1.

In another embodiment, the present invention also relates to catalytic domain variants of amino acids 19 to 397 of SEQ ID NO: 2 comprising a substitution, deletion, and/or insertion at one or more (e.g., several) positions. In one aspect, the number of amino acid substitutions, deletions and/or insertions introduced into the sequence of amino acids 19 to 397 of SEQ ID NO: 2 is 10, e.g., 1, 2, 3, 4, 5, 6, 8, or 9.

The catalytic domain according to the invention may further comprise or be fused to a cellulose binding domain.

Binding Domains

In one embodiment, the present invention also relates to cellulose binding domains having a sequence identity to amino acids 444 to 477 of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%. In one aspect, the cellulose binding domains comprise amino acid sequences that differ by no more than 10 amino acids, e.g., 1, 2, 3, 4, 5, 6, 7, 8, or 9, from amino acids 444 to 477 of SEQ ID NO: 2.

The cellulose binding domain preferably comprises or consists of amino acids 444 to 477 of SEQ ID NO: 2 or an allelic variant thereof; or is a fragment thereof having cellulose binding activity.

In another embodiment, the present invention also relates to cellulose binding domains encoded by polynucleotides that hybridize under high stringency conditions, or very high stringency conditions (as defined above) with (i) the nucleotides 1333 to 1431 of SEQ ID NO: 1, or (ii) the full-length complement of (i) (Sambrook et al., 1989, supra).

In another embodiment, the present invention also relates to cellulose binding domains encoded by polynucleotides having a sequence identity to nucleotides 1333 to 1431 of SEQ ID NO: 1 of at least 80%, at least 85%, at least 90%, at least 91%, at least 92%, at least 93%, at least 94%, at least 95%, at least 96%, at least 97%, at least 98%, at least 99%, or 100%.

The polynucleotide encoding the cellulose binding domain preferably comprises or consists of nucleotides 1333 to 1431 of SEQ ID NO: 1.

In another embodiment, the present invention also relates to cellulose binding domain variants of amino acids 444 to 477 of SEQ ID NO: 2 comprising a substitution, deletion, and/or insertion at one or more (e.g., several) positions. In one aspect, the number of amino acid substitutions, deletions and/or insertions introduced into the sequence of amino acids 444 to 477 of SEQ ID NO: 2 is 10, e.g., 1, 2, 3, 4, 5, 6, 8, or 9.

The binding domain according to the invention is in one embodiment operably linked to a catalytic domain, e.g., via a linker region. In one embodiment the linker comprises amino acids 398-443 of SEQ ID NO: 2.

A catalytic domain operably linked to the cellulose binding domain may be from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

Polynucleotides

The present invention also relates to isolated polynucleotides encoding an endoglucanase polypeptide, a catalytic domain, or a cellulose binding domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Talaromyces*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (VIIIa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals.

In these cases, the polynucleotide encoding the polypeptide would be operably linked with the regulatory sequence.

Expression Vectors

The present invention also relates to recombinant expression vectors comprising a polynucleotide of the present invention operably linked to one or more control sequences, e.g., a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces.* Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma.*

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus* equisubsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999,

*Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide. In a preferred aspect, the cell is a *Talaromyces* cell. In a more preferred aspect, the cell is a *Talaromyces leycettanus* cell. In a most preferred aspect, the cell is *Talaromyces leycettanus* CBS398.68.

The present invention also relates to methods of producing a polypeptide of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides having endoglucanase activity. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21:

415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Compositions

The present invention also relates to compositions comprising a polypeptide of the present invention. Preferably, the compositions are enriched in such a polypeptide. The term "enriched" indicates that the endoglucanase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as one or more (e.g., several) enzymes selected from the group consisting of a cellulase, a hemicellulase, GH61 polypeptide, an expansin, an esterase, a laccase, a ligninolytic enzyme, a pectinase, a peroxidase, a protease, and a swollenin. Preferably, the composition comprises the endoglucanase according to the invention and at least a cellobiohydrolase and a beta-glucosidase. In a most preferred embodiment the composition comprises the endoglucanase according to the invention and at least a cellobiohydrolase and a beta-glucosidase and a GH61 family polypeptide having cellulolytic enhancing activity.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Methods of Processing Cellulosic Material

The present invention also relates to methods for degrading or converting a cellulosic material, comprising: treating the cellulosic material with an enzyme composition in the presence of a polypeptide having endoglucanase activity of the present invention. In a preferred aspect, the method further comprises recovering the degraded or converted cellulosic material.

The present invention also relates to methods of producing a fermentation product, comprising: (a) saccharifying a cellulosic material with an enzyme composition in the presence of a polypeptide having endoglucanase activity of the present invention; (b) fermenting the saccharified cellulosic material with one or more (several) fermenting microorganisms to produce the fermentation product; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition in the presence of a polypeptide having endoglucanase activity of the present invention. In a preferred aspect, the fermenting of the cellulosic material produces a fermentation product. In another preferred aspect, the method further comprises recovering the fermentation product from the fermentation.

The methods of the present invention can be used to saccharify a cellulosic material to fermentable sugars and convert the fermentable sugars to many useful substances, e.g., fuel, potable ethanol, and/or fermentation products (e.g., acids, alcohols, ketones, gases, and the like). The production of a desired fermentation product from cellulosic material typically involves pretreatment, enzymatic hydrolysis (saccharification), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF); hybrid hydrolysis and co-fermentation (HHCF); and direct microbial conversion (DMC). SHF uses separate process steps to first enzymatically hydrolyze cellulosic material to fermentable sugars, e.g., glucose, cellobiose, cellotriose, and pentose sugars, and then ferment the fermentable sugars to ethanol. In SSF, the enzymatic hydrolysis of cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan and Himmel, 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (several) steps where the same organism is used to produce the enzymes for conversion of the cellulosic material to fermentable sugars and to convert the fermentable sugars into a final product (Lynd et al., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Corazza et al., 2003, Optimal control in fed-batch reactor for the cellobiose hydrolysis, *Acta Scientiarum. Technology* 25: 33-38; Gusakov and Sinitsyn, 1985, Kinetics of the enzymatic hydrolysis of cellulose: 1. A mathematical model for a batch reactor process, *Enz. Microb. Technol.* 7: 346-352), an attrition reactor (Ryu and Lee, 1983, Bioconversion of waste cellulose by using an attrition bioreactor, *Biotechnol. Bioeng.* 25: 53-65), or a reactor with intensive stirring induced by an electromagnetic field (Gusakov et al., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment. In practicing the methods of the present invention, any pretreatment process known in the art can be used to disrupt plant cell wall components of cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, cellulosic material is heated to disrupt the plant cell wall components, including lignin, hemicellulose, and cellulose to make the cellulose and other fractions, e.g., hemicellulose, accessible to enzymes. Cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* 105-108: 69-85, and Mosier et al., 2005, *Bioresource Technology* 96: 673-686, and U.S. Published Application No. 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: Cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the cellulosic material, e.g., pretreated, is hydrolyzed to break down cellulose and alternatively also hemicellulose to fermentable sugars, such as glucose, cellobiose, xylose, xylulose, arabinose, mannose, galactose, and/or soluble oligosaccharides. The hydrolysis is performed enzymatically by an enzyme composition in the presence of a polypeptide having endoglucanase activity of the present invention. The composition can further comprise one or more (several) hemicellulolytic or xylan degrading enzymes. The enzymes of the compositions can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 96 hours, more preferably about 16 to about 72 hours, and most preferably about 24 to about 48 hours. The temperature is in the range of preferably about 25° C. to about 70° C., more preferably about 30° C. to about 65° C., and more preferably about 40° C. to about 60° C., in particular about 50° C. The pH is in the range of preferably about 3 to about 8, more preferably about 3.5 to about 7, and most preferably about 4 to about 6, in particular about pH 5. The dry solids content is in the range of preferably about 5 to about 50 wt %, more preferably about 10 to about 40 wt %, and most preferably about 20 to about 30 wt %.

The enzyme composition preferably comprises enzymes having cellulolytic activity and/or xylan degrading activity. In one aspect, the enzyme composition comprises one or more (several) cellulolytic enzymes. In another aspect, the enzyme composition comprises one or more (several) xylan degrading enzymes. In another aspect, the enzyme composition comprises one or more (several) cellulolytic enzymes and one or more (several) xylan degrading enzymes.

The one or more (several) cellulolytic enzymes are preferably selected from the group consisting of an endoglucanase, a cellobiohydrolase, and a beta-glucosidase. The one or more (several) xylan degrading enzymes are preferably selected from the group consisting of a xylanase, an acetyxylan esterase, a feruloyl esterase, an arabinofuranosidase, a xylosidase, and a glucuronidase.

In another aspect, the enzyme composition further or even further comprises a polypeptide having cellulolytic enhancing activity (see, for example, WO 2005/074647, WO 2005/074656, and WO 2007/089290). In another aspect, the enzyme composition may further or even further comprise one or more (several) additional enzyme activities to improve the degradation of the cellulose-containing material. Preferred additional enzymes are hemicellulases (e.g., alpha-D-glucuronidases, alpha-L-arabinofuranosidases, endo-mannanases, beta-mannosidases, alpha-galactosidases, endo-alpha-L-arabinanases, beta-galactosidases), carbohydrate-esterases (e.g., acetyl-xylan esterases, acetyl-mannan esterases, ferulic acid esterases, coumaric acid esterases, glucuronoyl esterases), pectinases, proteases, ligninolytic enzymes (e.g., laccases, manganese peroxidases, lignin peroxidases, $H_2O_2$-producing enzymes, oxidoreductases), expansins, swollenins, or mixtures thereof. In the methods of the present invention, the additional enzyme(s) can be added prior to or during fermentation, e.g., during saccharification or during or after propagation of the fermenting microorganism(s).

One or more (several) components of the enzyme composition may be wild-type proteins, recombinant proteins, or a combination of wild-type proteins and recombinant proteins. For example, one or more (several) components may be native proteins of a cell, which is used as a host cell to express recombinantly one or more (several) other components of the enzyme composition. One or more (several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use in the processes described herein, such as, for example, a crude fermentation broth with or without cells removed, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having endoglucanase activity depend on several factors including, but not limited to, the mixture of component cellulolytic enzymes, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic enzyme(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another preferred aspect, an effective amount of polypeptide(s) having endoglucanase activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another preferred aspect, an effective amount of polypeptide(s) having endoglucanase activity to cellulolytic enzyme(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic enzyme(s).

The enzymes can be derived or obtained from any suitable origin, including, bacterial, fungal, yeast, plant, or mammalian origin. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having cellulolytic enzyme activity or xylan degrading activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having cellulolytic enzyme activity or xylan degrading activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having cellulolytic enzyme activity or xylan degrading activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having cellulolytic enzyme activity or xylan degrading activity.

In another preferred aspect, the polypeptide is a *Streptococcus equisimilis, Streptococcus pyogenes, Streptococcus uberis*, or *Streptococcus equi* subsp. *Zooepidemicus* polypeptide having cellulolytic enzyme activity or xylan degrading activity.

In another preferred aspect, the polypeptide is a *Streptomyces achromogenes, Streptomyces avermitilis, Streptomyces coelicolor, Streptomyces griseus*, or *Streptomyces lividans* polypeptide having cellulolytic enzyme activity or xylan degrading activity.

The polypeptide having cellulolytic enzyme activity or xylan degrading activity may also be a fungal polypeptide, and more preferably a yeast polypeptide such as a *Candida, Kluyveromyces, Pichia, Saccharomyces, Schizosaccharomyces*, or *Yarrowia* polypeptide having cellulolytic enzyme activity or xylan degrading activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having cellulolytic enzyme activity or xylan degrading activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having cellulolytic enzyme activity or xylan degrading activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having cellulolytic enzyme activity or xylan degrading activity.

Chemically modified or protein engineered mutants of polypeptides having cellulolytic enzyme activity or xylan degrading activity may also be used.

One or more (several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

Examples of commercial cellulolytic protein preparations suitable for use in the present invention include, for example, CELLIC™ Ctec (Novozymes A/S), CELLUCLAST™ (Novozymes A/S), NOVOZYM™ 188 (Novozymes A/S), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, more preferably from about 0.025 to about 4.0 wt % of solids, and most preferably from about 0.005 to about 2.0 wt % of solids. The cellulase enzymes are added in amounts effective from about 0.001 to about 5.0 wt % of solids, more preferably from about 0.025 to about 4.0 wt % of solids, and most preferably from about 0.005 to about 2.0 wt % of solids.

Examples of bacterial endoglucanases that can be used in the methods of the present invention as an additional endoglucanase, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used as an additional endoglucanase in the methods of the present invention, include, but are not limited to, a *Trichoderma reesei* endoglucanase I (Penttila et al., 1986, *Gene* 45: 253-263; GENBANK™ accession no. M15665); *Trichoderma reesei* endoglucanase II (Saloheimo, et al., 1988, *Gene* 63:11-22; GENBANK™ accession no. M19373); *Trichoderma reesei* endoglucanase III (Okada et al., 1988, *Appl. Environ. Microbiol.* 64: 555-563; GENBANK™ accession no. AB003694); and *Trichoderma reesei* endoglucanase V (Saloheimo et al., 1994, *Molecular Microbiology* 13: 219-228; GENBANK™ accession no. Z33381); *Aspergillus* aculeatus endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); Melanocarpus albomyces endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase; basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase); *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase (GENBANK™ accession no. M15665).

Examples of cellobiohydrolases useful in the methods of the present invention include, but are not limited to, *Trichoderma reesei* cellobiohydrolase I; *Trichoderma reesei* cellobiohydrolase II; *Humicola insolens* cellobiohydrolase I, *Myceliophthora thermophila* cellobiohydrolase II, *Thielavia terrestris* cellobiohydrolase II (CEL6A), *Chaetomium thermophilum* cellobiohydrolase I, and *Chaetomium thermophilum* cellobiohydrolase II.

Examples of beta-glucosidases useful in the methods of the present invention include, but are not limited to, *Aspergillus oryzae* beta-glucosidase; *Aspergillus fumigatus* beta-glucosidase; *Penicillium brasilianum* IBT 20888 beta-glucosidase; *Aspergillus niger* beta-glucosidase; and *Aspergillus aculeatus* beta-glucosidase.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499. The *Penicillium brasilianum* polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

The beta-glucosidase may be a fusion protein. In one aspect, the beta-glucosidase is the *Aspergillus oryzae* beta-glucosidase variant BG fusion protein or the *Aspergillus oryzae* beta-glucosidase fusion protein obtained according to WO 2008/057637.

Other endoglucanases, cellobiohydrolases, and beta-glucosidases are disclosed in numerous Glycosyl Hydrolase families using the classification according to Henrissat, 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696.

Other cellulolytic enzymes that may be used in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/0076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 4,435,307, 5,457,046, 5,648,263, 5,686,593, 5,691,178, 5,763,254, and 5,776,757.

In the methods of the present invention, any GH61 polypeptide having cellulolytic enhancing activity can be used.

Examples of polypeptides having cellulolytic enhancing activity useful in the methods of the present invention include, but are not limited to, polypeptides having cellulolytic enhancing activity from *Thielavia terrestris* (WO 2005/074647); polypeptides having cellulolytic enhancing activity from *Thermoascus aurantiacus* (WO 2005/074656); polypeptides having cellulolytic enhancing activity from *Trichoderma reesei* (WO 2007/089290); and polypeptides having cellulolytic enhancing activity from *Myceliophthora thermophila* (WO 2009/085935; WO 2009/085859; WO 2009/085864; WO 2009/085868).

Examples of commercial xylan degrading enzyme preparations suitable for use in the present invention include, for example, SHEARZYME™ (Novozymes A/S), CELLIC™ Htec (Novozymes A/S), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, *Aspergillus aculea-*

*tus* xylanase (GeneSeqP:AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number 092458), *Talaromyces emersonii* (SwissProt accession number Q8x212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number QOUHJ1), and *Humicola insolens* DSM 1800 acetylxylan esterase (WO 2009/073709).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number alcc12), *Trichoderma reesei* alpha-glucuronidase (Uniprot accession number Q99024), *Talaromyces emersonii* alpha-glucuronidase (UniProt accession number Q8x211), *Aspergillus niger* alpha-glucuronidase (Uniprot accession number Q96WX9), *Aspergillus terreus* alpha-glucuronidase (SwissProt accession number Q0CJP9), and *Aspergillus fumigatus* alpha-glucuronidase (SwissProt accession number Q4WW45).

The enzymes and proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and 011 is, D. F., *Biochemical Engineering Fundamentals*, McGraw-Hill Book Company, NY, 1986).

The fermentation can be any method of cultivation of a cell resulting in the expression or isolation of an enzyme. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation. The fermentable sugars obtained from the hydrolyzed cellulosic material can be fermented by one or more (several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment $C_6$ sugars include bacterial and fungal organisms, such as yeast. Preferred yeast includes strains of the *Saccharomyces* spp., preferably *Saccharomyces cerevisiae*.

Examples of fermenting organisms that can ferment $C_5$ sugars include bacterial and fungal organisms, such as yeast. Preferred $C_5$ fermenting yeast include strains of *Pichia*, preferably *Pichia stipitis*, such as *Pichia stipitis* CBS 5773; strains of *Candida*, preferably *Candida boidinii*, *Candida brassicae*, *Candida sheatae*, *Candida diddensii*, *Candida pseudotropicalis*, or *Candida utilis*.

Other fermenting organisms include strains of *Zymomonas*, such as *Zymomonas mobilis*; *Hansenula*, such as *Hansenula anomala*; *Kluyveromyces*, such as *K. fragilis*; *Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas* mobilis. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMO-SACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces* sp.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded cellulosic material and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, The biotechnological production of sorbitol, *Appl. Microbiol. Biotechnol.* 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36(6-7): 41-47; and Gunaseelan, 1997, *Biomass and Bioenergy* 13(1-2): 83-114, Anaerobic digestion of biomass for methane production: A review.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Signal Peptide and Propeptide

The present invention also relates to an isolated polynucleotide encoding a signal peptide comprising or consisting of amino acids 1 to 18 of SEQ ID NO: 2. The present invention also relates to an isolated polynucleotide encoding a signal peptide and a propeptide comprising or consisting of amino acids 1 to 18 of SEQ ID NO: 2. The polynucleotides may further comprise a gene encoding a protein, which is operably linked to the signal peptide and/or propeptide. The protein is preferably foreign to the signal peptide and/or propeptide. In one aspect, the polynucleotide encoding the signal peptide is nucleotides 1 to 54 of SEQ ID NO: 1.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

The gene may be obtained from any prokaryotic, eukaryotic, or other source.

The present invention is further described by the following examples that should not be construed as limiting the scope of the invention.

List of Preferred Embodiments

Embodiment 1. An isolated polypeptide having endoglucanase activity, selected from the group consisting of:
  (a) a polypeptide having at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide of SEQ ID NO: 2;
  (b) a polypeptide encoded by a polynucleotide that hybridizes under medium-high stringency conditions, high stringency conditions, or very high stringency conditions with (i) the mature polypeptide coding sequence of SEQ ID NO: 1, or (ii) the full-length complement of (i);
  (c) a polypeptide encoded by a polynucleotide having at least 75%, at least 80%, at least 85%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;
  (d) a variant of the mature polypeptide of SEQ ID NO: 2 comprising a substitution, deletion, and/or insertion at one or several positions; and (e) a fragment of the polypeptide of (a), (b), (c), or (d) that has endoglucanase activity.

Embodiment 2. The polypeptide of embodiment 1, having at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2.

Embodiment 3. The polypeptide of embodiment 1 or 2, which is encoded by a polynucleotide that hybridizes under medium-high stringency conditions, high stringency conditions, or very high stringency conditions with (i) the mature polypeptide coding sequence of SEQ ID NO: 1, or (ii) the full-length complement of (i).

Embodiment 4. The polypeptide of any of embodiments 1-3, which is encoded by a polynucleotide having at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1.

Embodiment 5. The polypeptide of any of embodiments 1-4, comprising or consisting of SEQ ID NO: 2 or the mature polypeptide of SEQ ID NO: 2.

Embodiment 6. The polypeptide of embodiment 5, wherein the mature polypeptide is amino acids 19 to 477 of SEQ ID NO: 2.

Embodiment 7. An isolated polypeptide comprising a catalytic domain selected from the group consisting of:
  (a) a catalytic domain having at least 80% sequence identity to amino acids 19 to 397 of SEQ ID NO: 2;
  (b) a catalytic domain encoded by a polynucleotide that hybridizes under high, or very high stringency conditions with (i) nucleotides 55 to 1191 of SEQ ID NO: 1, or (ii) the full-length complement of (i);
  (c) a catalytic domain encoded by a polynucleotide having at least 80% sequence identity to the catalytic domain of SEQ ID NO: 1;
  (d) a variant of amino acids 19 to 397 of SEQ ID NO: 2 comprising a substitution, deletion, and/or insertion at one or several positions; and
  (e) a fragment of the catalytic domain of (a), (b), (c), or (d) that has endoglucanase activity.

Embodiment 8. The polypeptide of embodiment 7, further comprising a cellulose binding domain.

Embodiment 9. An isolated polypeptide comprising a cellulose binding domain operably linked to a catalytic domain, wherein the binding domain is selected from the group consisting of:
  (a) a cellulose binding domain having at least 80% sequence identity to amino acids 444 to 477 of SEQ ID NO: 2;
  (b) a cellulose binding domain encoded by a polynucleotide that hybridizes under high, or very high stringency conditions with (i) nucleotides 1333 to 1431 of SEQ ID NO: 1, or (ii) the full-length complement of (i);
  (c) a cellulose binding domain encoded by a polynucleotide having at least 80% sequence identity to nucleotides 1333 to 1431 of SEQ ID NO: 1;
  (d) a variant of amino acids 444 to 477 of SEQ ID NO: 2 comprising a substitution, deletion, and/or insertion at one or several positions; and
  (e) a fragment of (a), (b), (c), (d) or (e) that has cellulose binding activity.

Embodiment 10. The polypeptide of embodiment 9, wherein the catalytic domain is obtained from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase.

Embodiment 11. A composition comprising the polypeptide of any of embodiments 1-10.

Embodiment 12. The composition of embodiment 11, further comprising a cellobiohydrolase, and a beta-glucosidase.

Embodiment 13. A method for degrading or converting a cellulosic material, comprising: treating the cellulosic material with an enzyme composition in the presence of the polypeptide having endoglucanase activity of any of embodiments 1-8.

Embodiment 14. The method of embodiment 13, wherein the cellulosic material is pretreated.

Embodiment 15. The method of embodiment 13 or 14, wherein the enzyme composition comprises one or more enzymes selected from the group consisting of a cellulase, a polypeptide having cellulolytic enhancing activity, a hemicellulase, an esterase, a protease, a laccase, or a peroxidase.

Embodiment 16. The method of embodiment 15, wherein the cellulase is one or more enzymes selected from the group consisting of an endoglucanase, a cellobiohydrolase, and a beta-glucosidase.

Embodiment 17. The method of embodiment 15, wherein the hemicellulase is one or more enzymes selected from the group consisting of a xylanase, an acetyxylan esterase, a feruloyl esterase, an arabinofuranosidase, a xylosidase, and a glucuronidase.

Embodiment 18. The method of any of embodiments 13-17, further comprising recovering the degraded cellulosic material.

Embodiment 19. The method of embodiment 18, wherein the degraded cellulosic material is a sugar.

Embodiment 20. The method of embodiment 19, wherein the sugar is selected from the group consisting of glucose, xylose, mannose, galactose, and arabinose.

Embodiment 21. A method for producing a fermentation product, comprising:
(a) saccharifying a cellulosic material with an enzyme composition in the presence of the polypeptide having endoglucanase activity of any of embodiments 1-8;
(b) fermenting the saccharified cellulosic material with one or more fermenting microorganisms to produce the fermentation product; and
(c) recovering the fermentation product from the fermentation.

Embodiment 22. The method of embodiment 21, wherein the cellulosic material is pretreated.

Embodiment 23. The method of embodiment 21 or 22, wherein the enzyme composition comprises one or more enzymes selected from the group consisting of a cellulase, a polypeptide having cellulolytic enhancing activity, a hemicellulase, an esterase, a protease, a laccase, or a peroxidase.

Embodiment 24. The method of embodiment 23, wherein the cellulase is one or more enzymes selected from the group consisting of an endoglucanase, a cellobiohydrolase, and a beta-glucosidase.

Embodiment 25. The method of embodiment 23, wherein the hemicellulase is one or more enzymes selected from the group consisting of a xylanase, an acetyxylan esterase, a feruloyl esterase, an arabinofuranosidase, a xylosidase, and a glucuronidase.

Embodiment 26. The method of any of embodiments 21-25, wherein steps (a) and (b) are performed simultaneously in a simultaneous saccharification and fermentation.

Embodiment 27. The method of any of embodiments 21-26, wherein the fermentation product is an alcohol, an organic acid, a ketone, an amino acid, or a gas.

Embodiment 28. A method of fermenting a cellulosic material, comprising: fermenting the cellulosic material with one or more fermenting microorganisms, wherein the cellulosic material is saccharified with an enzyme composition in the presence of a polypeptide having endoglucanase activity of any of embodiments 1-8.

Embodiment 29. The method of embodiment 28, wherein the fermenting of the cellulosic material produces a fermentation product.

Embodiment 30. The method of embodiment 29, further comprising recovering the fermentation product from the fermentation.

Embodiment 31. The method of any of embodiments 28-30, wherein the cellulosic material is pretreated before saccharification.

Embodiment 32. The method of any of embodiments 28-31, wherein the enzyme composition comprises one or more enzymes selected from the group consisting of a cellulase, a polypeptide having cellulolytic enhancing activity, a hemicellulase, an esterase, a protease, a laccase, or a peroxidase.

Embodiment 33. The method of embodiment 32, wherein the cellulase is one or more enzymes selected from the group consisting of an endoglucanase, a cellobiohydrolase, and a beta-glucosidase.

Embodiment 34. The method of embodiment 32, wherein the hemicellulase is one or more enzymes selected from the group consisting of a xylanase, an acetyxylan esterase, a feruloyl esterase, an arabinofuranosidase, a xylosidase, and a glucuronidase.

Embodiment 35. The method of any of embodiments 29-34, wherein the fermentation product is an alcohol, an organic acid, a ketone, an amino acid, or a gas.

Embodiment 36. An isolated polynucleotide encoding the polypeptide of any of embodiments 1-10.

Embodiment 37. A nucleic acid construct or expression vector comprising the polynucleotide of embodiment 36 operably linked to one or more control sequences that direct the production of the polypeptide in an expression host.

Embodiment 38. A recombinant host cell comprising the polynucleotide of embodiment 36 operably linked to one or more control sequences that direct the production of the polypeptide.

Embodiment 39. A method of producing the polypeptide of any of embodiments 1-10, comprising:
(a) cultivating a cell, which in its wild-type form produces the polypeptide, under conditions conducive for production of the polypeptide; and
(b) recovering the polypeptide.

Embodiment 40. A method of producing a polypeptide having endoglucanase activity, comprising:
(a) cultivating the host cell of embodiment 38 under conditions conducive for production of the polypeptide; and
(b) recovering the polypeptide.

Embodiment 41. A transgenic plant, plant part or plant cell transformed with a polynucleotide encoding the polypeptide of any of embodiments 1-10.

Embodiment 42. A method of producing a polypeptide having endoglucanase activity, comprising:
(a) cultivating the transgenic plant or plant cell of embodiment 41 under conditions conducive for production of the polypeptide; and
(b) recovering the polypeptide.

Embodiment 43. An isolated signal peptide comprising or consisting of amino acids 1 to 18 of SEQ ID NO: 2.

Embodiment 44. An isolated polynucleotide encoding a signal peptide comprising or consisting of amino acids 1 to 18 of SEQ ID NO: 2.

Embodiment 45. A nucleic acid construct or expression vector comprising a gene encoding a protein operably linked to the polynucleotide of embodiment 44, wherein the gene is foreign to the polynucleotide encoding the signal peptide.

Embodiment 46. A recombinant host cell comprising a gene encoding a protein operably linked to the polynucleotide of embodiment 44, wherein the gene is foreign to the polynucleotide encoding the signal peptide.

Embodiment 47. A method of producing a protein, comprising:
(a) cultivating a recombinant host cell comprising a gene encoding a protein operably linked to the polynucleotide of embodiment 44, wherein the gene is foreign to the polynucleotide encoding the signal peptide, under conditions conducive for production of the protein; and
(b) recovering the protein.

EXAMPLES

Materials

Chemicals used as buffers and substrates were commercial products of at least reagent grade.

Strains

*Talaromyces leycettanus* Strain CBS398.68 was used as the source of a polypeptide having endoglucanase activity. *Aspergillus oryzae* MT3568 strain was used for expression of the *Talaromyces leycettanus* gene encoding the polypeptide having endoglucanase activity. *A. oryzae* MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene.

Media and Solutions

YP+2% glucose medium was composed of 1% yeast extract, 2% peptone and 2% glucose.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter. The medium was sterilized by autoclaving at 15 psi for 15 minutes (Bacteriological Analytical Manual, 8th Edition, Revision A, 1998).

COVE sucrose plates were composed of 342 g Sucrose (Sigma S-9378), 20 g Agar powder, 20 ml Cove salt solution (26 g $MgSO_4.7H_2O$, 26 g KCL, 26 g $KH_2PO_4$, 50 ml Cove trace metal solution) and deionized water to 1 liter), and deionized water to 1 liter). The medium was sterilized by autoclaving at 15 psi for 15 minutes (Bacteriological Analytical Manual, 8th Edition, Revision A, 1998). The medium was cooled to 60° C. and added 10 mM acetamide, 15 mM CsCl, Triton X-100 (50 µl/500 ml)).

Cove trace metal solution was composed of 0.04 g $Na_2B_4O_7.10H_2O$, 0.4 g $CuSO_4.5H_2O$, 1.2 g $FeSO_4.7H_2O$, 0.7 g $MnSO_4.H_2O$, 0.8 g $Na_2MoO_4.2H_2O$, 10 g $ZnSO_4.7H_2O$, and deionized water to 1 liter.

Dap-4C medium was composed of 20 g Dextrose, 10 g Maltose, 11 g $MgSO_4.7H_2O$, 1 g $KH_2PO_4$, 2 g Citric Acid, 5.2 g $K_3PO_4.H_2O$, 0.5 g Yeast Extract (Difco), 1 ml Dowfax 63N10 (Dow Chemical Company), 0.5 ml KU6 trace metals solution, 2.5 g $CaCO_3$, and deionized water to 1 liter. The medium was sterilized by autoclaving at 15 psi for 15 minutes (Bacteriological Analytical Manual, 8th Edition, Revision A, 1998). Before use, Dap-4C medium was added 3.5 ml sterile 50% $(NH_4)_2HPO_4$ and 5 ml sterile 20% Lactic Acid per 150 ml medium.

KU6 trace metals solution was composed of 0.13 g $NiCl_2$, 2.5 g $CuSO_4.5H_2O$, 13.9 g $FeSO_4.7H_2O$, 8.45 g $MnSO_4.H_2O$, 6.8 g $ZnCl_2$, 3 g Citric Acid, and deionized water to 1 liter.

Example 1

Source of DNA Sequence Information for *Talaromyces leycettanus* Strain CBS398.68

Genomic sequence information was generated by Illumina DNA sequencing at the Beijing Genome Institute (BGI) in Beijing, China from genomic DNA isolated from *Talaromyces leycettanus* Strain CBS398.68. A preliminary assembly of the genome was analyzed using the Pedant-Pro™ Sequence Analysis Suite (Biomax Informatics AG, Martinsried, Germany). Gene models constructed by the software were used as a starting point for detecting GH7 homologues in the genome. More precise gene models were constructed manually using multiple known GH7 protein sequences as a guide.

Example 2

*Talaromyces Leycettanus* Strain CBS398.68 Genomic DNA Extraction

To generate genomic DNA for PCR amplification, *Talaromyces leycettanus* Strain CBS398.68 was propagated on PDA agar plates by growing at 26° C. for 7 days. Spores harvested from the PDA plates were used to inoculate 25 ml of YP+2% glucose medium in a baffled shake flask and incubated at 30° C. for 72 hours with agitation at 85 rpm.

Genomic DNA was isolated according to a modified DNeasy Plant Maxi kit protocol (Qiagen Danmark, Copenhagen, Denmark). The fungal material from the above culture was harvested by centrifugation at 14,000×g for 2 minutes. The supernatant was removed and the 0.5 g of the pellet was frozen in liquid nitrogen with quartz sand and grinded to a fine powder in a pre-chilled mortar. The powder was transferred to a 15 ml centrifuge tube and added 5 ml buffer AP1 (preheated to 65° C.) and 10 µl RNase A stock solution (100 mg/ml) followed by vigorous vortexing. After incubation for 10 minutes at 65° C. with regular inverting of the tube, 1.8 ml buffer AP2 was added to the lysate by gentle mixing followed by incubation on ice for 10 min. The lysate was then centrifugated at 3000×g for 5 minutes at room temperature and the supernatant was decanted into a QIAshredder maxi spin column placed in a 50 ml collection tube. This was followed by centrifugation at 3000×g for 5 minutes at room temperature. The flow-through was transferred into a new 50 ml tube and added 1.5 volumes of buffer AP3/E followed by vortexing. 15 ml of the sample was transferred into a DNeasy Maxi spin column placed in a 50 ml collection tube and centrifuged at 3000×g for 5 minutes at room temperature. The flow-through was discarded and 12 ml buffer AW was added to the DNeasy Maxi spin column placed in a 50 ml collection tube and centrifuged at 3000×g for 10 minutes at room temperature. After discarding the flow-through, centrifugation was repeated to dispose of the remaining alcohol. The DNeasy Maxi spin column was transferred to a new 50 ml tube and 0.5 ml buffer AE (preheated to 70° C.) was added. After incubation for 5 minutes at room temperature, the sample was eluded by centrifugation at 3000×g for 5 minutes at room temperature. Elution was repeated with an additional 0.5 ml buffer AE and the eluates were combined. The concentration of the harvested DNA was measured by a UV spectrophotometer at 260 nm.

Example 3

Construction of an *Aspergillus oryzae* Expression Vector Containing *Talaromyces Leycettanus* Strain CBS398.68 Genomic Sequence Encoding a Family GH7 Polypeptide Having Endoglucanase Activity Two synthetic oligonucleotide primers shown below were designed to PCR amplify the *Talaromyces leycettanus* Strain CBS398.68 P23YSZ gene from the genomic DNA prepared in Example 2. An IN-FUSION™ Cloning Kit (BD Biosciences, Palo Alto, Calif., USA) was used to clone the fragment directly into the expression vector pDau109 (WO 2005/042735).

```
F-P23YSZ
                                                (SEQ ID NO: 3)
5'-ACACAACTGGGGATCCACCATGGCTCCAAAACTCGCT-3'

R-P23YSZ
                                                (SEQ ID NO: 4)
5'-CCCTCTAGATCTCGAGCGCCTCCAACATTGTCGATT-3'
```

Bold letters represent gene sequence. The underlined sequence is homologous to the insertion sites of pDau 109.

An MJ Research PTC-200 DNA engine was used to perform the PCR reaction. A Phusion® High-Fidelity PCR Kit (Finnzymes Oy, Espoo, Finland) was used for the PCR amplification. The PCR reaction was composed of 5 µl of 5×HF buffer (Finnzymes Oy, Espoo, Finland), 0.5 µl of dNTPs (10 mM), 0.5 µl of Phusion® DNA polymerase (0.2 units/µl) (Finnzymes Oy, Espoo, Finland), 1 µl of primer F—P23YSZ (5 µM), 1 µl of primer R—P23YSZ (5 µM), 0.5 µl of *Talaromyces leycettanus* genomic DNA (100 ng/µl), and 16.5 µl of deionized water in a total volume of 25 µl. The PCR conditions were 1 cycle at 95° C. for 2 minutes. 35 cycles each at 98° C. for 10 seconds, 60° C. for 30 seconds, and 72° C. for 2 minutes; and 1 cycle at 72° C. for 10 minutes. The sample was then held at 12° C. until removed from the PCR machine.

The reaction products were isolated by 1.0% agarose gel electrophoresis using 40 mM Tris base, 20 mM sodium acetate, 1 mM disodium EDTA (TAE) buffer where a 1513 bp product band was excised from the gel and purified using an illustra GFX® PCR DNA and Gel Band Purification Kit (GE Healthcare Life Sciences, Brondby, Denmark) according to the manufacturer's instructions. The fragment was then cloned into Barn HI and Xho I digested pDau109 using an IN-FUSION™ Cloning Kit resulting in plasmid pP23YSZ. Cloning of the P23YSZ gene into Barn HI-Xho I digested pDau109 resulted in the transcription of the *Talaromyces leycettanus* P23YSZ gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The cloning protocol was performed according to the IN-FUSION™ Cloning Kit instructions generating a P23YSZ GH7 construct. The treated plasmid and insert were transformed into One Shot® TOP10F" Chemically Competent *E. coli* cells (Invitrogen, Carlsbad, Calif., USA) according to the manufacturer's protocol and plated onto LB plates supplemented with 0.1 mg of ampicillin per ml. After incubating at 37° C. overnight, colonies were seen growing under selection on the LB ampicillin plates. Four colonies transformed with the P23YSZ GH7 construct were cultivated in LB medium supplemented with 0.1 mg of ampicillin per ml and plasmid was isolated with a QIAprep Spin Miniprep Kit (QIAGEN Inc., Valencia, Calif., USA) according to the manufacturer's protocol.

Isolated plasmids were sequenced with vector primers and P23YSZ gene specific primers in order to determine a representative plasmid expression clone that was free of PCR errors.

Example 4

Characterization of the *Talaromyces leycettanus* CBS398.68 Genomic Sequence Encoding a P23YSZ GH7 Polypeptide Having Endoglucanase Activity DNA sequencing of the *Talaromyces leycettanus* CBS398.68 P23YSZ GH7 genomic clone was performed with an Applied Biosystems Model 3700 Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA). The sequence obtained was identical to the sequence from the BGI.

The nucleotide sequence and deduced amino acid sequence of the *Talaromyces leycettanus* P23YSZ gene is shown in SEQ ID NO: 1 and SEQ ID NO: 2, respectively. The coding sequence is 1434 bp including the stop codon. The encoded predicted protein is 477 amino acids. Using the SignalP program (Nielsen et al., 1997, *Protein Engineering* 10:1-6), a signal peptide of 18 residues was predicted. The predicted mature protein contains 459 amino acids with a predicted molecular mass of 48 kDa and an isoelectric pH of 4.16.

A comparative pairwise global alignment of amino acid sequences was determined using the Needleman and Wunsch algorithm (Needleman and Wunsch, 1970, *J. Mol. Biol.* 48: 443-453) with gap open penalty of 10, gap extension penalty of 0.5, and the EBLOSUM62 matrix. The alignment showed that the deduced amino acid sequence of the *Talaromyces leycettanus* gene encoding the P23YSZ GH7 polypeptide having endoglucanase activity shares 74.2% identity (excluding gaps) to the deduced amino acid sequence of a predicted GH7 family protein from *Neosartorya fischeri* (accession number SWISSPROT:A1 DKY9) with endoglucanase activity.

Example 5

Expression of the *Talaromyces leycettanus* GH7 Endoglucanase P23YSZ

The expression plasmid pP23YSZ was transformed into *Aspergillus oryzae* MT3568. *Aspergillus oryzae* MT3568 is an AMDS (acetamidase) disrupted derivative of JaL355 (WO 2002/40694) in which pyrG auxotrophy was restored in the process of knocking out the A, oryzae acetamidase (AMDS) gene. MT3568 protoplasts are prepared according to the method of European Patent, EP0238023, pages 14-15, which are incorporated herein by reference.

Transformants were purified on COVE sucrose selection plates through single conidia prior to sporulating them on PDA plates. Production of the *Talaromyces leycettanus* GH7 polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, Calif., USA) by Coomassie staining. One transformant was selected for further work and designated *Aspergillus oryzae* 90.3.

For larger scale production, *Aspergillus oryzae* 90.3 spores were spread onto a PDA plate and incubated for five days at 37° C. The confluent spore plate was washed twice with 5 ml of 0.01% TWEEN® 20 to maximize the number of spores collected. The spore suspension was then used to inoculate twenty five 500 ml flasks containing 100 ml of Dap-4C medium. The culture was incubated at 30° C. with constant shaking at 100 rpm. At day four post-inoculation, the culture broth was collected by filtration through a bottle top MF75 Supor MachV 0.2 µm PES filter (Thermo Fisher Scientific, Roskilde, Denmark). Fresh culture broth from this transformant produced a band of GH7 protein of approximately 70 kDa. The identity of this band as the *Talaromyces leycettanus* GH7 polypeptide was verified by peptide sequencing.

Example 6

Alternative Method for Producing the *Talaromyces leycettanus* GH7 Endoglucanase P23YSZ Based on the nucleotide sequence identified as SEQ ID NO: 1, a synthetic gene can be obtained from a number of vendors such as Gene Art (GENEART AG BioPark, Josef-Engert-Str. 11, 93053, Regensburg, Germany) or DNA 2.0 (DNA2.0, 1430 O'Brien Drive, Suite E, Menlo Park, Calif. 94025, USA). The synthetic gene can be designed to incorporate additional DNA sequences such as restriction sites or homologous recombination regions to facilitate cloning into an expression vector.

Using the two synthetic oligonucleotide primers F—P23YSZ and F—P23YSZ described above, a simple PCR reaction can be used to amplify the full-length open reading frame from the synthetic gene of SEQ ID NO: 1. The gene can then be cloned into an expression vector for example as described above and expressed in a host cell, for example in *Aspergillus oryzae* as described above.

Example 7

Purification of the *Talaromyces leycettanus* GH7 Endoglucanase P23YSZ 1000 ml broth of the *Aspergillus oryzae* expression strain 90.3 was adjusted to pH 7.0 and filtrated on 0.22 µm PES filter (Thermo Fisher Scientific, Roskilde, Denmark). Following, the filtrate was added 1.8 M ammonium sulphate. The filtrate was loaded onto a Phenyl Sepharose™ 6 Fast Flow column (high sub) (GE Healthcare, Piscataway, N.J., USA) (column volume 60 mL) equilibrated with 1.8 M ammonium sulphate pH 7.0, 25 mM HEPES pH7.0. After application the column was washed with 3 column volumes of 1.0 M ammonium sulphate and the protein eluted following with 5 column volumes of 25 mM HEPES pH 7.0 at a flow rate of 15 ml/min. Fractions of 10 mL were collected and analyzed by SDS-page. The fractions were pooled and applied to a Sephadex™ G-25 (medium) (GE Healthcare, Piscataway, N.J., USA) column equilibrated in 25 mM HEPES pH 7.0. The fractions were applied to a SOURCE™ 15Q (GE Healthcare, Piscataway, N.J., USA) column equilibrated in 25 mM HEPES pH 7.0 (column volume 60 mL). After application the column was washed with 3 column volumes equilibration buffer and bound proteins were eluted with a linear gradient over 20 column volumes from 0-500 mM sodium chloride. Fractions of 10 ml were collected and analyzed by SDS-page, and fractions with the protein were pooled to a final volume of 148 ml. The protein concentration was determined by A280/A260 absorbance.

Example 8

Endoglucanase Assay

The concentrate is assayed for endoglucanase activity by a microtiter plate assay as described below. A solution of 0.2% AZCL-HE-Cellulose (Megazyme International Ireland, Ltd., Bray, Co. Wicklow, Ireland) is made in a 0.1 M sodium acetate pH 5.5 buffer with stirring. The solution is distributed under stirring to a microtiter plate (200 µl to each well). Then 20 µl of enzyme sample is added and incubated in an EPPEN-DORF® THERMOMIXER® (Eppendorf AG, Hamburg, Germany) for 20 minutes at 50° C. and 650 rpm. A denatured enzyme sample (100° C. boiling for 20 minutes) is used as blank. After incubation the colored solution is separated from the solid substrate by centrifugation at 3000 rpm for 5 minutes at 4° C. A 150 µl sample of supernatant is transferred to a microtiter plate; and the absorbance is measured at 595 nm using a SPECTRAMAX® M2 Multi-Mode Microplate Reader (Molecular Devices, Beijing, China).

Example 9

Pretreated Corn Stover Hydrolysis Assay

Corn stover was pretreated at the U.S. Department of Energy National Renewable Energy Laboratory (NREL) using 1.4 wt % sulfuric acid at 165° C. and 107 psi for 8 minutes. The water-insoluble solids in the pretreated corn stover (PCS) contained 56.5% cellulose, 4.6% hemicellulose and 28.4% lignin. Cellulose and hemicellulose were determined by a two-stage sulfuric acid hydrolysis with subsequent analysis of sugars by high performance liquid chromatography using NREL Standard Analytical Procedure #002. Lignin was determined gravimetrically after hydrolyzing the cellulose and hemicellulose fractions with sulfuric acid using NREL Standard Analytical Procedure #003.

Unmilled, unwashed PCS (whole slurry PCS) was prepared by adjusting the pH of PCS to 5.0 by addition of 10 M NaOH with extensive mixing, and then autoclaving for 20 minutes at 120° C. The dry weight of the whole slurry PCS was 29%. The PCS was used unwashed or washed with water. Milled unwashed PCS (dry weight 32.35%) was prepared by milling whole slurry PCS in a Cosmos ICMG 40 wet multi-utility grinder (EssEmm Corporation, Tamil Nadu, India). Milled washed PCS (dry weight 32.35%) was prepared in the same manner, with subsequent washing with deionized water and decanting off the supernatant fraction repeatedly.

The hydrolysis of PCS was conducted using 2.2 ml deep-well plates (Axygen, Union City, Calif., USA) in a total reaction volume of 1.0 ml. The hydrolysis was performed with 50 mg of insoluble PCS solids per ml of 50 mM sodium acetate pH 5.0 buffer containing 1 mM manganese sulfate and various protein loadings of various enzyme compositions (expressed as mg protein per gram of cellulose). Enzyme compositions were prepared and then added simultaneously to all wells in a volume ranging from 50 µl to 200 µl, for a final volume of 1 ml in each reaction. The plate was then sealed using an ALPS-300™ plate heat sealer (Abgene, Epsom, United Kingdom), mixed thoroughly, and incubated at a specific temperature for 72 hours. All experiments reported were performed in triplicate.

Following hydrolysis, samples were filtered using a 0.45 µm MULTISCREEN® 96-well filter plate (Millipore, Bedford, Mass., USA) and filtrates analyzed for sugar content as described below. When not used immediately, filtered aliquots were frozen at −20° C. The sugar concentrations of samples diluted in 0.005 M $H_2SO_4$ were measured using a 4.6×250 mm AMINEX® HPX-87H column (Bio-Rad Laboratories, Inc., Hercules, Calif., USA) by elution with 0.05% w/w benzoic acid-0.005 M $H_2SO_4$ at 65° C. at a flow rate of 0.6 ml per minute, and quantitation by integration of the glucose, cellobiose, and xylose signals from refractive index detection (CHEMSTATION®, AGILENT® 1100 HPLC, Agilent Technologies, Santa Clara, Calif., USA) calibrated by pure sugar samples. The resultant glucose and cellobiose equivalents were used to calculate the percentage of cellulose conversion for each reaction.

Glucose, cellobiose, and xylose were measured individually. Measured sugar concentrations were adjusted for the appropriate dilution factor. The net concentrations of enzymatically-produced sugars from unwashed PCS were determined by adjusting the measured sugar concentrations for corresponding background sugar concentrations in unwashed PCS at zero time point. All HPLC data processing was performed using MICROSOFT EXCEL™ software (Microsoft, Richland, Wash., USA).

The degree of cellulose conversion to glucose was calculated using the following equation: % conversion=(glucose concentration/glucose concentration in a limit digest)×100. In order to calculate % conversion, a 100% conversion point was set based on a cellulase control (100 mg of *Trichoderma reesei* cellulase per gram cellulose), and all values were divided by this number and then multiplied by 100. Triplicate data points were averaged and standard deviation was calculated.

Example 10

Preparation of an Enzyme Composition

The *Aspergillus fumigatus* GH7A cellobiohydrolase I (SEQ ID NO: 5 [DNA sequence] and SEQ ID NO: 6 [deduced amino acid sequence]) was prepared recombinantly in *Aspergillus oryzae* as described in WO 2011/057140. The filtered broth of *Aspergillus fumigatus* GH7A cellobiohydrolase I was concentrated and buffer exchanged using a tangential flow concentrator (Pall Filtron, Northborough, Mass., USA) equipped with a 10 kDa polyethersulfone membrane (Pall Filtron, Northborough, Mass., USA) with 20 mM Tris-HCl pH 8.0. The desalted broth of *Aspergillus fumigatus* GH7A cellobiohydrolase I was purified over a Q SEPHAROSE™ ion exchange chromatography column (GE Healthcare, Piscataway, N.J., USA) in 20 mM Tris-HCl pH 8, over a linear 0 to 1 M NaCl gradient. Fractions were collected and fractions containing the cellobiohydrolase I cellulase were pooled based on 8-16% CRITERION® Stain-free SDS-PAGE (Bio-Rad Laboratories, Inc., Hercules, Calif., USA).

Preparation of *Aspergillus fumigatus* NN055679 cellobiohydrolase II. The *Aspergillus fumigatus* GH6A cellobiohydrolase II (SEQ ID NO: 7 [DNA sequence] and SEQ ID NO: 8 [deduced amino acid sequence]) was prepared recombinantly in *Aspergillus oryzae* as described in WO 2011/057140. The filtered broth of *Aspergillus fumigatus* GH6A cellobiohydrolase II was buffer exchanged into 20 mM Tris pH 8.0 using a 400 ml SEPHADEX™ G-25 column (GE Healthcare, United Kingdom) according to the manufacturer's instructions. The fractions were pooled and adjusted to 1.2 M ammonium sulphate-20 mM Tris pH 8.0. The equilibrated protein was loaded onto a PHENYL SEPHAROSE™ 6 Fast Flow column (high sub) (GE Healthcare, Piscataway, N.J., USA) equilibrated in 20 mM Tris pH 8.0 with 1.2 M ammonium sulphate, and bound proteins were eluted with 20 mM Tris pH 8.0 with no ammonium sulphate. The fractions were pooled.

Preparation of *Penicillium* sp. (*emersonii*) GH61A polypeptide having cellulolytic enhancing activity. The *Penicillium* sp. (*emersonii*) GH61A polypeptide (SEQ ID NO: 9 [DNA sequence] and SEQ ID NO: 10 [deduced amino acid sequence]) was recombinantly prepared according to WO 2011/041397. The *Penicillium* sp. (*emersonii*) GH61A polypeptide gene was purified according to WO 2011/041397.

Preparation of *Aspergillus fumigatus* NN055679 GH10 xylanase. The *Aspergillus fumigatus* GH10 xylanase (xyn3) (SEQ ID NO: 11 [DNA sequence] and SEQ ID NO: 12 [deduced amino acid sequence]) was prepared recombinantly according to WO 2006/078256 using *Aspergillus oryzae* BECh2 (WO 2000/39322) as a host. The filtered broth of *Aspergillus fumigatus* NN055679 GH10 xylanase (xyn3) was desalted and buffer-exchanged into 50 mM sodium acetate pH 5.0 using a HIPREP® 26/10 Desalting Column (GE Healthcare, Piscataway, N.J., USA) according to the manufacturer's instructions.

Preparation of *Aspergillus fumigatus* NN055679 Cel3A beta-glucosidase. (SEQ ID NO: 13 [DNA sequence] and SEQ ID NO: 14 [deduced amino acid sequence]) was recombinantly prepared according to WO 2005/047499 using *Aspergillus oryzae* as a host. The filtered broth was adjusted to pH 8.0 with 20% sodium acetate, which made the solution turbid. To remove the turbidity, the solution was centrifuged (20000×g, 20 minutes), and the supernatant was filtered through a 0.2 µm filtration unit (Nalgene, Rochester, N.Y., USA). The filtrate was diluted with deionized water to reach the same conductivity as 50 mM Tris/HCl, pH 8.0. The adjusted enzyme solution was applied to a Q SEPHAROSE™ Fast Flow column (GE Healthcare, Piscataway, N.J., USA) equilibrated in 50 mM Tris-HCl, pH 8.0 and eluted with a linear gradient from 0 to 500 mM sodium chloride. Fractions were pooled and treated with 1% (w/v) activated charcoal to remove color from the beta-glucosidase pool. The charcoal was removed by filtration of the suspension through a 0.2 µm filtration unit (Nalgene, Rochester, N.Y., USA). The filtrate was adjusted to pH 5.0 with 20% acetic acid and diluted 10 times with deionized water. The adjusted filtrate was applied to a SP SEPHAROSE™ Fast Flow column (GE Healthcare, Piscataway, N.J., USA) equilibrated in 10 mM succinic acid, pH 5.0 and eluted with a linear gradient from 0 to 500 mM sodium chloride.

Preparation of *Aspergillus fumigatus* NN051616 GH3 beta-xylosidase. The *Aspergillus fumigatus* GH3 beta-xylosidase (SEQ ID NO: 15 [DNA sequence] and SEQ ID NO: 16 [deduced amino acid sequence]) was prepared recombinantly in *Aspergillus oryzae* as described in WO 2011/057140. The filtered broth of *Aspergillus fumigatus* NN051616 GH3 beta-xylosidase was desalted and buffer-exchanged into 50 mM sodium acetate pH 5.0 using a HIPREP® 26/10 Desalting Column (GE Healthcare, Piscataway, N.J., USA) according to the manufacturer's instructions.

The protein concentration for each of the monocomponents described above was determined using a Microplate BCA™ Protein Assay Kit (Thermo Fischer Scientific, Waltham, Mass., USA) in which bovine serum albumin was used as a protein standard. An enzyme composition was composed of each monocomponent, prepared as described above, as follows: 37% *Aspergillus fumigatus* Cel7A cellobiohydrolase I, 25% *Aspergillus fumigatus* Cel6A cellobiohydrolase II, 15% *Penicillium emersonii* GH61A polypeptide having cellulolytic enhancing activity, 5% *Aspergillus fumigatus* GH10 xylanase, 5% *Aspergillus fumigatus* beta-glucosidase, and 3% *Aspergillus fumigatus* beta-xylosidase. The enzyme composition is designated herein as "enzyme composition without endoglucanase".

Example 11

Preparation of *Trichoderma reesei* Endoglucanase II

Preparation of *Trichoderma reesei* GH5 endoglucanase II. The *Trichoderma reesei* GH5 endoglucanase II (SEQ ID NO: 17 [DNA sequence] and SEQ ID NO: 18 [deduced amino acid sequence]) was prepared recombinantly according to WO 2011/057140 using *Aspergillus oryzae* as a host. The filtered broth of *Trichoderma reesei* GH5 endoglucanase II was desalted and buffer-exchanged into 20 mM Tris pH 8.0 using tangential flow (10K membrane, Pall Filtron, Northborough, Mass., USA) according to the manufacturer's instructions.

Example 12

Effect of *Talaromyces leycettanus* Family GH7 Endoglucanase I (P23YSZ) in the Hydrolysis of Milled Unwashed PCS at 50-65° C. By an Enzyme Composition The *Talaromyces leycettanus* Family GH7 endoglucanase I (P23YSZ) was evaluated in an enzyme composition without endoglucanase at 50° C., 55° C., 60° C., and 65° C. using milled unwashed PCS as a substrate. The enzyme composition without endoglucanase (Example 10) was added to PCS hydrolysis reactions at 2.7 mg total protein per g cellulose, and the hydrolysis results were compared with the results for a similar enzyme composition with and without added GH7 endoglucanase (3.0 mg protein per g cellulose).

The assay was performed as described in Example 9. The 1 ml reactions with milled unwashed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

As shown in Table 1, below, the enzyme composition that included the *Talaromyces leycettanus* Family GH7 endoglucanase I (P23YSZ) significantly outperformed the enzyme composition without endoglucanase (2.7 mg protein/g cellulose and 3.0 mg protein/g cellulose) at 50° C., 55° C., 60° C., and 65° C. (as the degree of cellulose conversion to glucose for the *Talaromyces leycettanus* Family GH7 endoglucanase I (P23YSZ) was higher than the enzyme composition without endoglucanase at 50° C., 55° C., 60° C., and 65° C.). The results in Table 1, below, show that the enzyme composition that included *Talaromyces leycettanus* Family GH7 endoglucanase I (P23YSZ) performed about the same as the enzyme composition that included *Trichoderma reesei Family GH*5 endoglucanase II at 60° C. and 65° C. (as the degree of cellulose conversion to glucose for *Talaromyces leycettanus* Family GH7 endoglucanase I (P23YSZ) was about the same as the enzyme composition containing *Trichoderma reesei* Family GH5 endoglucanase II at 60° C. and 65° C.).

TABLE 1

| Enzyme Composition | % Cellulose to Glucose Conversion | | | |
|---|---|---|---|---|
| | 50° C. | 55° C. | 60° C. | 65° C. |
| Enzyme Composition w/o EG (2.7 mg/g) | 32.02 | 34.92 | 31.81 | 26.49 |
| Enzyme Composition w/o EG (3.0 mg/g) | 33.33 | 36.85 | 33.42 | 28.55 |
| Enzyme Composition (2.7 mg/g) with *Trichoderma reesei* EGII (.3 mg/g) | 56.06 | 58.49 | 45.99 | 37.94 |
| Enzyme Composition (2.7 mg/g) with *Talaromyces leycettanus* EGI (.3 mg/g) | 51.40 | 53.59 | 45.17 | 38.65 |

Example 13

Evaluation of Two Endoglucanases on Milled Washed PCS at 50-65° C.

Two endoglucanases were evaluated at 1 mg protein per g cellulose at 50° C., 55° C., 60° C., and 65° C. using milled washed PCS as a substrate with 1 mg protein per g cellulose of *Aspergillus fumigatus* Family GH3 beta-glucosidase. The following endoglucanases were tested: *Talaromyces leycettanus* Family GH7 endoglucanase I (P23YSZ) and *Trichoderma reesei* Family GH5 endoglucanase II.

The assay was performed as described in Example 9. The 1 ml reactions with milled washed PCS (5% insoluble solids) were conducted for 72 hours in 50 mM sodium acetate pH 5.0 buffer containing 1 mM manganese sulfate. All reactions were performed in triplicate and involved single mixing at the beginning of hydrolysis.

The results shown in Table 2, below, demonstrated that at 50° C., 55° C., 60° C., and 65° C. the *Talaromyces leycettanus* Family GH7 endoglucanase I (P23YSZ) had higher cellulose to glucose conversion than that of the *Trichoderma reesei* Family GH5 endoglucanase II.

TABLE 2

| Enzyme Composition | % Cellulose to Glucose Conversion | | | |
|---|---|---|---|---|
| | 50° C. | 55° C. | 60° C. | 65° C. |
| Trichoderma reesei EGII (1 mg/g) + *Aspergillus fumigatus* bG (1 mg/g) | 3.91 | 4.01 | 4.14 | 3.51 |
| *Talaromyces leycettanus* EGI (1 mg/g) + *Aspergillus fumigatus* bG (1 mg/g) | 4.08 | 4.33 | 4.62 | 4.24 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A nucleic acid construct comprising a polynucleotide encoding a polypeptide having endoglucanase activity, wherein the polynucleotide is operably linked to one or more heterologous control sequences that direct production of the polypeptide in an expression host, and wherein the polypeptide is selected from:
    (a) a polypeptide having at least 95% sequence identity to amino acids 19 to 477 of SEQ ID NO: 2;
    (b) a polypeptide encoded by a polynucleotide that hybridizes under very high stringency conditions with (i) nucleotides 55 to 1434 of SEQ ID NO: 1, or (ii) the full-length complement of (i), wherein very high stringency conditions are defined as prehybridization and hybridization at 42° C. in 5×SSPE, 0.3% SDS, 200 µg/ml sheared and denatured salmon sperm DNA, and 50% formamide and washing three times each for 15 minutes using 2×SSC, 0.2% SDS at 70° C.; and
    (c) a polypeptide encoded by a polynucleotide having at least 95% sequence identity to nucleotides 55 to 1434 of SEQ ID NO: 1.

2. The nucleic acid construct of claim 1, wherein the polypeptide having endoglucanase activity comprises or consists of amino acids 19 to 477 of SEQ ID NO: 2.

3. A nucleic acid construct comprising a polynucleotide encoding a polypeptide having a catalytic domain, wherein the polynucleotide is operably linked to one or more heterologous control sequences that direct production of the polypeptide in an expression host, and wherein the catalytic domain is selected from:
    (a) a catalytic domain having at least 95% sequence identity to amino acids 19 to 397 of SEQ ID NO: 2;
    (b) a catalytic domain encoded by a polynucleotide that hybridizes under very high stringency conditions with (i) nucleotides 55 to 1191 of SEQ ID NO: 1, or (ii) the full-length complement of (i), wherein very high stringency conditions are defined as prehybridization and hybridization at 42° C. in 5×SSPE, 0.3% SDS, 200µg/ml sheared and denatured salmon sperm DNA, and 50% formamide and washing three times each for 15 minutes using 2×SSC, 0.2% SDS at 70° C.; and
    (c) a catalytic domain encoded by a polynucleotide having at least 95% sequence identity nucleotides 55 to 1191 of SEQ ID NO: 1.

4. The nucleic acid construct of claim 3, wherein the polypeptide further comprises a cellulose binding domain.

5. A nucleic acid construct comprising a polynucleotide encoding a polypeptide having a cellulose binding domain linked to a catalytic domain, wherein the polynucleotide is operably linked to one or more heterologous control sequences that direct production of the polypeptide in an expression host, and wherein the binding domain is selected from:
    (a) a cellulose binding domain having at least 95% sequence identity to amino acids 444 to 477 of SEQ ID NO: 2;
    (b) a cellulose binding domain encoded by a polynucleotide that hybridizes under very high stringency conditions with (i) nucleotides 1333 to 1431 of SEQ ID NO: 1, or (ii) the full-length complement of (i), wherein very high stringency conditions are defined as prehybridization and hybridization at 42° C. in 5×SSPE, 0.3% SDS, 200µg/ml sheared and denatured salmon sperm DNA, and 50% formamide and washing three times each for 15 minutes using 2×SSC, 0.2% SDS at 70° C.; and
    (c) a cellulose binding domain encoded by a polynucleotide having at least 95% sequence identity to nucleotides 1333 to 1431 of SEQ ID NO: 1.

6. A method for degrading or converting a cellulosic material, said method comprising:
    (i) treating the cellulosic material with an enzyme composition in the presence of a polypeptide having endoglucanase activity; and
    (ii) recovering the degraded cellulosic material;
wherein the polypeptide having endoglucanase activity is selected from:
    (a) a polypeptide having at least 95% sequence identity to amino acids 19 to 477 of SEQ ID NO: 2;
    (b) a polypeptide encoded by a polynucleotide that hybridizes under very high stringency conditions with (i) nucleotides 55 to 1434 of SEQ ID NO: 1, or (ii) the full-length complement of (i), wherein very high stringency conditions are defined as prehybridization and hybridization at 42° C. in 5×SSPE, 0.3% SDS, 200 µg/ml sheared and denatured salmon sperm DNA, and 50% formamide and washing three times each for 15 minutes using 2×SSC, 0.2% SDS at 70° C.; and
    (c) a polypeptide encoded by a polynucleotide having at least 95% sequence identity to nucleotides 55 to 1434 of SEQ ID NO: 1.

7. A method for producing a fermentation product, said method comprising:
    (i) saccharifying a cellulosic material with an enzyme composition in the presence of a polypeptide having endoglucanase activity;
    (ii) fermenting the saccharified cellulosic material with one or more fermenting microorganisms to produce the fermentation product; and
    (iii) recovering the fermentation product from the fermentation;
wherein the polypeptide having endoglucanase activity is selected from:
    (a) a polypeptide having at least 95% sequence identity to amino acids 19 to 477 of SEQ ID NO: 2;
    (b) a polypeptide encoded by a polynucleotide that hybridizes under very high stringency conditions with (i) nucleotides 55 to 1434 of SEQ ID NO: 1, or (ii) the full-length complement of (i), wherein very high stringency conditions are defined as prehybridization and hybridization at 42° C. in 5×SSPE, 0.3% SDS, 200 µg/ml sheared and denatured salmon sperm DNA, and 50% formamide and washing three times each for 15 minutes using 2×SSC, 0.2% SDS at 70° C.; and
    (c) a polypeptide encoded by a polynucleotide having at least 95% sequence identity to nucleotides 55 to 1434 of SEQ ID NO: 1.

8. A method of fermenting a cellulosic material, said method comprising:
  (i) fermenting the cellulosic material with one or more fermenting microorganisms, wherein the cellulosic material is saccharified with an enzyme composition in the presence of a polypeptide having endoglucanase activity, and wherein the fermenting of the cellulosic material produces a fermentation product; and
  (ii) recovering the fermentation product from the fermentation;
wherein the polypeptide having endoglucanase activity is selected from:
  (a) a polypeptide having at least 95% sequence identity to amino acids 19 to 477 of SEQ ID NO: 2;
  (b) a polypeptide encoded by a polynucleotide that hybridizes under very high stringency conditions with (i) nucleotides 55 to 1434 of SEQ ID NO: 1, or (ii) the full-length complement of (i), wherein very high stringency conditions are defined as prehybridization and hybridization at 42° C. in 5×SSPE, 0.3% SDS, 200 μg/ml sheared and denatured salmon sperm DNA, and 50% formamide and washing three times each for 15 minutes using 2×SSC, 0.2% SDS at 70° C.; and
  (c) a polypeptide encoded by a polynucleotide having at least 95% sequence identity nucleotides 55 to 1434 of SEQ ID NO: 1.

9. An expression vector comprising the nucleic acid construct of claim 1.

10. An isolated recombinant host cell comprising the nucleic acid construct of claim 1.

11. A method of producing a polypeptide having endoglucanase activity, comprising:
  (a) cultivating the host cell of claim 10 under conditions conducive for production of the polypeptide; and
  (b) recovering the polypeptide.

12. A nucleic acid construct or expression vector comprising a gene encoding a protein operably linked to a polynucleotide encoding a signal peptide, wherein the signal peptide comprises amino acids 1 to 18 of SEQ ID NO: 2, and wherein the gene is foreign to the polynucleotide encoding the signal peptide.

13. An isolated recombinant host cell comprising the nucleic acid construct or expression vector of claim 12.

14. A method of producing a protein, comprising:
  (a) cultivating the recombinant host cell of claim 13, under conditions conducive for production of the protein; and
  (b) recovering the protein.

15. The nucleic acid construct of claim 1, wherein the polypeptide having endoglucanase activity comprises or consists of SEQ ID NO: 2.

16. The nucleic acid construct of claim 1, wherein the polypeptide having endoglucanase activity has at least 95% sequence identity to amino acids 19 to 477 of SEQ ID NO: 2.

17. The nucleic acid construct of claim 1, wherein the polypeptide having endoglucanase activity has at least 97% sequence identity to amino acids 19 to 477 of SEQ ID NO: 2.

18. The nucleic acid construct of claim 1, wherein the polypeptide having endoglucanase activity is a variant comprising a substitution, deletion, or insertion of one or more amino acids of amino acids 19 to 477 of SEQ ID NO: 2.

19. The nucleic acid construct of claim 3, wherein the catalytic domain has at least 95% sequence identity to amino acids 19 to 397 of SEQ ID NO: 2.

20. The nucleic acid construct of claim 3, wherein the catalytic domain has at least 97% sequence identity to amino acids 19 to 397 of SEQ ID NO: 2.

21. The nucleic acid construct of claim 3, wherein the catalytic domain comprises amino acids 19 to 397 of SEQ ID NO: 2.

22. An expression vector comprising the nucleic acid construct of claim 3.

23. An isolated recombinant host cell comprising the nucleic acid construct of claim 3.

24. The nucleic acid construct of claim 5, wherein the cellulose binding domain has at least 95% sequence identity to amino acids 444 to 477 of SEQ ID NO: 2.

25. The nucleic acid construct of claim 5, wherein the cellulose binding domain has at least 97% sequence identity to amino acids 444 to 477 of SEQ ID NO: 2.

26. The nucleic acid construct of claim 5, wherein the cellulose binding domain comprises amino acids 444 to 477 of SEQ ID NO: 2.

27. An expression vector comprising the nucleic acid construct of claim 5.

28. An isolated recombinant host cell comprising the nucleic acid construct of claim 5.

29. The method of claim 6, wherein the polypeptide having endoglucanase activity has at least 97% sequence identity to amino acids 19 to 477 of SEQ ID NO: 2.

* * * * *

SEQUENCE LISTING

<160> NUMBER OF SEQ ID NOS: 18

<210> SEQ ID NO 1
<211> LENGTH: 1464
<212> TYPE: DNA

<213> ORGANISM: Talaromyces leycettanus

<400> SEQUENCE: 1

```
atggctccaa aactcgcttt cacagctctg gctgttcttc ctattgtcgc tgcccagcag      60
attggcacaa cccctgagac tcaccccctcg ctgacgacct ggaaatgtac gaccggaggc    120
gggtgtgtcg cgcaggatac ctctattgtc atcgactggg gtaccattg gatccatcag     180
accggaactg atgtttcgtg tacgacttct aacggggtga actcgacctt gtgcccaaac    240
gaggcgacat gctcccagaa ctgcgtgatt gagggagcaa actacaccag cagcggcgtt    300
gcaacgtcgg gcagctccct gactctccat caatatgtcc agagcaatgg tcagaccagc    360
aacgcgtccc cacgtgtcta tctcttgggc cccgatggga actacgtcat gctccagctc    420
cttggccagg agctgagctt tgatgtggat gtctccacgc tggtctgcgg agagaacggt    480
gcactgtatc tctccgagat ggacgccacc ggtggtcgca gccagtacaa tcctggagga    540
gccaactatg ttctggata ctgtgatgct caatgccccg tcgagacctg atgaacggc     600
accctcaaca ccagtggaca gggttactgc tgcaatgaaa tggatctctg ggaggcgaat    660
gcgtacgcaa cggcctacac gccccatccg tgcggcaatg gatcgtgcga caagagtgga    720
tgcggttttca atccctacgc cttgggagac acagcactact acggacccgg tttgacggtc    780
gatacatcca agcccttac cgtgacaacg cagttcatca ccaacgacgg caccaccacc    840
ggaaccctca ccgagatccg ccgccagtac atccagaatg caaggtgat tgcaaacgcc    900
gtgtcctcgt ctggcgttga ctccatcacc gaatcgtggt gtgtatccgt ggatggagcc    960
gccgcctcct tcggcggcct gaccacgatg ggtcaggctc tgagccgcgg tatggtgcta   1020
gttttcagca tctggaacga caacagccag ttcatgaact ggcttgacag cggaagttcc   1080
ggtccttgca gcagcaccgc cggcaacccg gccaccattg aagcacagga ccccggtacc   1140
tatgtcacct tctctaacat caagtgggga gacatcggat ccacgttcca atcctcttcg   1200
ggtggatcga gttcgacatc gacgacgacg tcgaccactt ccaagcagac gagtaccacc   1260
actaccacga ccacgaccac gaccaccaag cctacaagca ccacgaccac agctactggc   1320
gcgactcaga ctcactgggg acaatgcgga ggagagactt ggactggccc aaccgtttgt   1380
gctccgccgt actcgtgcca gacccagaac ccatggtacg ctcagtgctt gtaaaaacgg   1440
tcaaaatcga caatgttgga ggcg                                          1464
```

<210> SEQ ID NO 2
<211> LENGTH: 477
<212> TYPE: PRT
<213> ORGANISM: Talaromyces leycettanus

<400> SEQUENCE: 2

```
Met Ala Pro Lys Leu Ala Phe Thr Ala Leu Ala Val Leu Pro Ile Val
1               5                   10                  15

Ala Ala Gln Gln Ile Gly Thr Thr Pro Glu Thr His Pro Ser Leu Thr
            20                  25                  30

Thr Trp Lys Cys Thr Thr Gly Gly Gly Cys Val Ala Gln Asp Thr Ser
        35                  40                  45

Ile Val Ile Asp Trp Gly Tyr His Trp Ile His Gln Thr Gly Thr Asp
    50                  55                  60

Val Ser Cys Thr Thr Ser Asn Gly Val Asn Ser Thr Leu Cys Pro Asn
65                  70                  75                  80

Glu Ala Thr Cys Ser Gln Asn Cys Val Ile Glu Gly Ala Asn Tyr Thr
                85                  90                  95
```

Ser Ser Gly Val Ala Thr Ser Gly Ser Ser Leu Thr Leu His Gln Tyr
            100                 105                 110

Val Gln Ser Asn Gly Gln Thr Ser Asn Ala Ser Pro Arg Val Tyr Leu
            115                 120                 125

Leu Gly Pro Asp Gly Asn Tyr Val Met Leu Gln Leu Leu Gly Gln Glu
        130                 135                 140

Leu Ser Phe Asp Val Asp Val Ser Thr Leu Val Cys Gly Glu Asn Gly
145                 150                 155                 160

Ala Leu Tyr Leu Ser Glu Met Asp Ala Thr Gly Gly Arg Ser Gln Tyr
                165                 170                 175

Asn Pro Gly Gly Ala Asn Tyr Gly Ser Gly Tyr Cys Asp Ala Gln Cys
            180                 185                 190

Pro Val Glu Thr Trp Met Asn Gly Thr Leu Asn Thr Ser Gly Gln Gly
        195                 200                 205

Tyr Cys Cys Asn Glu Met Asp Leu Trp Glu Ala Asn Ala Tyr Ala Thr
210                 215                 220

Ala Tyr Thr Pro His Pro Cys Gly Asn Gly Ser Cys Asp Lys Ser Gly
225                 230                 235                 240

Cys Gly Phe Asn Pro Tyr Ala Leu Gly Asp His Ser Tyr Tyr Gly Pro
                245                 250                 255

Gly Leu Thr Val Asp Thr Ser Lys Pro Phe Thr Val Thr Thr Gln Phe
            260                 265                 270

Ile Thr Asn Asp Gly Thr Thr Gly Thr Leu Thr Glu Ile Arg Arg
        275                 280                 285

Gln Tyr Ile Gln Asn Gly Lys Val Ile Ala Asn Ala Val Ser Ser Ser
290                 295                 300

Gly Val Asp Ser Ile Thr Glu Ser Trp Cys Val Ser Val Asp Gly Ala
305                 310                 315                 320

Ala Ala Ser Phe Gly Gly Leu Thr Thr Met Gly Gln Ala Leu Ser Arg
                325                 330                 335

Gly Met Val Leu Val Phe Ser Ile Trp Asn Asp Asn Ser Gln Phe Met
            340                 345                 350

Asn Trp Leu Asp Ser Gly Ser Ser Gly Pro Cys Ser Ser Thr Ala Gly
        355                 360                 365

Asn Pro Ala Thr Ile Glu Ala Gln Asp Pro Gly Thr Tyr Val Thr Phe
370                 375                 380

Ser Asn Ile Lys Trp Gly Asp Ile Gly Ser Thr Phe Gln Ser Ser Ser
385                 390                 395                 400

Gly Gly Ser Ser Ser Thr Ser Thr Thr Thr Ser Thr Thr Ser Lys Gln
                405                 410                 415

Thr Ser Thr Thr Thr Thr Thr Thr Thr Thr Thr Thr Thr Lys Pro Thr
            420                 425                 430

Ser Thr Thr Thr Thr Ala Thr Gly Ala Thr Gln Thr His Trp Gly Gln
        435                 440                 445

Cys Gly Gly Glu Thr Trp Thr Gly Pro Thr Val Cys Ala Pro Pro Tyr
    450                 455                 460

Ser Cys Gln Thr Gln Asn Pro Trp Tyr Ala Gln Cys Leu
465                 470                 475

<210> SEQ ID NO 3
<211> LENGTH: 37
<212> TYPE: DNA
<213> ORGANISM: Artificial
<220> FEATURE:

<223> OTHER INFORMATION: PCR primer

<400> SEQUENCE: 3
acacaactgg ggatccacca tggctccaaa actcgct    37

<210> SEQ ID NO 4
<211> LENGTH: 36
<212> TYPE: DNA
<213> ORGANISM: Artificial
<220> FEATURE:
<223> OTHER INFORMATION: PCR primer

<400> SEQUENCE: 4
ccctctagat ctcgagcgcc tccaacattg tcgatt    36

<210> SEQ ID NO 5
<211> LENGTH: 1599
<212> TYPE: DNA
<213> ORGANISM: Aspergillus fumigatus

<400> SEQUENCE: 5
atgctggcct ccaccttctc ctaccgcatg tacaagaccg cgctcatcct ggccgccctt    60
ctgggctctg gccaggctca gcaggtcggt acttcccagg cggaagtgca tccgtccatg    120
acctggcaga gctgcacggc tggcggcagc tgcaccacca caacggcaa ggtggtcatc    180 gacgcgaact ggcgttgggt gcacaaagtc ggcgactaca ccaactgcta caccggcaac    240
acctgggaca cgactatctg ccctgacgat gcgacctgcg catccaactg cgcccttgag    300
ggtgccaact acgaatccac ctatggtgtg accgccagcg gcaattccct ccgcctcaac    360
ttcgtcacca ccagccagca agaagaacatt ggctcgcgtc tgtacatgat gaaggacgac    420
tcgacctacg agatgtttaa gctgctgaac caggagttca ccttcgatgt cgatgtctcc    480
aacctcccct gcggtctcaa cggtgctctg tactttgtcg ccatggacgc cgacggtggc    540
atgtccaagt acccaaccaa caaggccggt gccaagtacg gtactggata ctgtgactcg    600
cagtgccctc gcgacctcaa gttcatcaac ggtcaggcca acgtcgaagg gtggcagccc    660
tcctccaacg atgccaatgc gggtaccggc aaccacgggt cctgctgcgc ggagatggat    720
atctgggagg ccaacagcat ctccacggcc ttcacccccc atccgtgcga cacgcccggc    780
caggtgatgt gcaccggtga tgcctgcggt ggcacctaca gctccgaccg ctacggcggc    840
acctgcgacc ccgacggatg tgatttcaac tccttccgcc agggcaacaa gaccttctac    900
ggccctggca tgaccgtcga caccaagagc aagtttaccg tcgtcaccca gttcatcacc    960
gacgacggca cctccagcgg caccctcaag gagatcaagc gcttctacgt gcagaacggc    1020
aaggtgatcc ccaactcgga gtcgacctgg accggcgtca gcggcaactc catcaccacc    1080
gagtactgca ccgcccagaa gagcctgttc caggaccaga acgtcttcga aaagcacggc    1140
ggcctcgagg gcatgggtgc tgccctcgcc cagggtatgg ttctcgtcat gtccctgtgg    1200
gatgatcact cggccaacat gctctggctc gacagcaact cccgaccac tgcctcttcc    1260 accactcccg gcgtcgcccg tggtacctgc gacatctcct ccggcgtccc tgcggatgtc    1320
gaggcgaacc accccgacgc ctacgtcgtc tactccaaca tcaaggtcgg ccccatcggc    1380
tcgaccttca acagcggtgg ctcgaacccc ggtggcggaa ccaccacgac aactaccacc    1440
cagcctacta ccaccacgac cacggctgga aaccctggcg gcaccggagt cgcacagcac    1500
tatggccagt gtggtggaat cggatggacc ggacccacaa cctgtgccag cccttatacc    1560
tgccagaagc tgaatgatta ttactctcag tgcctgtag    1599

<210> SEQ ID NO 6
<211> LENGTH: 532
<212> TYPE: PRT
<213> ORGANISM: Aspergillus fumigatus

<400> SEQUENCE: 6

```
Met Leu Ala Ser Thr Phe Ser Tyr Arg Met Tyr Lys Thr Ala Leu Ile
 1               5                  10                  15

Leu Ala Ala Leu Leu Gly Ser Gly Gln Ala Gln Gln Val Gly Thr Ser
                20                  25                  30

Gln Ala Glu Val His Pro Ser Met Thr Trp Gln Ser Cys Thr Ala Gly
            35                  40                  45

Gly Ser Cys Thr Thr Asn Asn Gly Lys Val Val Ile Asp Ala Asn Trp
        50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
            100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
            180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
            260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
290                 295                 300

Thr Val Asp Thr Lys Ser Lys Phe Thr Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
            340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
```

```
            370             375             380
Met Gly Ala Ala Leu Ala Gln Gly Met Val Leu Val Met Ser Leu Trp
385             390             395             400

Asp Asp His Ser Ala Asn Met Leu Trp Leu Asp Ser Asn Tyr Pro Thr
            405             410             415

Thr Ala Ser Ser Thr Thr Pro Gly Val Ala Arg Gly Thr Cys Asp Ile
            420             425             430

Ser Ser Gly Val Pro Ala Asp Val Glu Ala Asn His Pro Asp Ala Tyr
        435             440             445

Val Val Tyr Ser Asn Ile Lys Val Gly Pro Ile Gly Ser Thr Phe Asn
450             455             460

Ser Gly Gly Ser Asn Pro Gly Gly Gly Thr Thr Thr Thr Thr Thr Thr
465             470             475             480

Gln Pro Thr Thr Thr Thr Thr Ala Gly Asn Pro Gly Gly Thr Gly
            485             490             495

Val Ala Gln His Tyr Gly Gln Cys Gly Gly Ile Gly Trp Thr Gly Pro
            500             505             510

Thr Thr Cys Ala Ser Pro Tyr Thr Cys Gln Lys Leu Asn Asp Tyr Tyr
            515             520             525

Ser Gln Cys Leu
    530
```

<210> SEQ ID NO 7
<211> LENGTH: 1713
<212> TYPE: DNA
<213> ORGANISM: Aspergillus fumigatus

<400> SEQUENCE: 7

```
atgaagcacc ttgcatcttc catcgcattg actctactgt tgcctgccgt gcaggcccag    60
cagaccgtat ggggccaatg tatgttctgg ctgtcactgg aataagactg tatcaactgc   120
tgatatgctt ctaggtggcg gccaaggctg gtctggcccg acgagctgtg ttgccggcgc   180
agcctgtagc acactgaatc cctgtatgtt agatatcgtc ctgagtggag acttatactg   240
acttccttag actacgctca gtgtatcccg ggagccaccg cgacgtccac caccctcacg   300
acgacgacgg cggcgacgac gacatcccag accaccacca aacctaccac gactggtcca   360
actacatccg cacccaccgt gaccgcatcc ggtaacccct tcagcggcta ccagctgtat   420
gccaacccct actactcctc cgaggtccat actctggcca tgccttctct gcccagctcg   480
ctgcagccca aggctagtgc tgttgctgaa gtgccctcat tgtttggct gtaagtggcc    540
ttatcccaat actgagacca actctctgac agtcgtagcg acgttgccgc caaggtgccc   600
actatgggaa cctacctggc cgacattcag gccaagaaca aggccggcgc caaccctcct   660
atcgctggta tcttcgtggt ctacgacttg ccggaccgtg actgcgccgc tctggccagt   720
aatggcgagt actcaattgc caacaacggt gtggccaact acaaggcgta cattgacgcc   780
atccgtgctc agctggtgaa gtactctgac gttcacacca cctcgtcat cggtaggccg    840
tacacctccg ttgcgcgccg cctttctctg acatcttgca gaacccgaca gcttggccaa   900
cctggtgacc aacctcaacg tcgccaaatg cgccaatgcg cagagcgcct acctggagtg   960
tgtcgactat gctctgaagc agctcaacct gcccaacgtc gccatgtacc tcgacgcagg  1020
tatgcctcac ttcccgcatt ctgtatccct tccagacact aactcatcag gccatgcggg  1080
ctggctcgga tggcccgcca acttgggccc cgccgcaaca ctcttcgcca agtctacac   1140
cgacgcgggt tcccccgcgg ctgttcgtgg cctggccacc aacgtcgcca actacaacgc  1200
```

```
ctggtcgctc agtacctgcc cctcctacac ccagggagac cccaactgcg acgagaagaa   1260
gtacatcaac gccatggcgc tcttctcaa ggaagccggc ttcgatgccc acttcatcat    1320
ggatacctgt aagtgcttat tccaatcgcc gatgtgtgcc gactaatcaa tgtttcagcc   1380
cggaatggcg tccagcccac gaagcaaaac gcctggggtg actggtgcaa cgtcatcggc   1440
accggcttcg tgttcgccc tcgactaac accggcgatc cgctccagga tgcctttgtg     1500
tggatcaagc ccgtgggaga gagtgatggc acgtccaact cgacttcccc ccggtatgac   1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713

<210> SEQ ID NO 8
<211> LENGTH: 454
<212> TYPE: PRT
<213> ORGANISM: Aspergillus fumigatus

<400> SEQUENCE: 8

Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
                20                  25                  30

Ser Gly Pro Thr Ser Cys Val Ala Gly Ala Ala Cys Ser Thr Leu Asn
            35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
```

```
                275                 280                 285
Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
        355                 360                 365

Gln Asn Ala Trp Gly Asp Trp Cys Asn Val Ile Gly Thr Gly Phe Gly
    370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450

<210> SEQ ID NO 9
<211> LENGTH: 835
<212> TYPE: DNA
<213> ORGANISM: Penicillium emersonii

<400> SEQUENCE: 9
atgctgtctt cgacgactcg caccctcgcc tttacaggcc ttgcgggcct tctgtccgct        60
cccctggtca aggcccatgg ctttgtccag ggcattgtca tcggtgacca attgtaagtc       120
cctctcttgc agttctgtcg attaactgct ggactgcttg cttgactccc tgctgactcc       180
caacagctac agcgggtaca tcgtcaactc gttcccctac gaatccaacc cacccccgt        240 catcggctgg ccacgaccg ccaccgacct gggcttcgtc gacggcacag ataccaagg         300 cccggacatc atctgccacc ggaatgcgac gcccgcgccg ctgacagccc ccgtggccgc       360
cggcggcacc gtcgagctgc agtggacgcc gtggccggac agccaccacg acccgtcat        420 cacctacctg gcgccgtgca acggcaactg ctcgaccgtc gacaagacga cgctggagtt       480
cttcaagatc gaccagcagg cctgatcga cgacacgagc ccgccgggca cctgggcgtc        540
ggacaacctc atcgccaaca caatagctg accgtcacc attcccaaca gcgtcgcccc        600
cggcaactac gtcctgcgcc acgagatcat cgccctgcac tcggccaaca acaaggacgg       660
cgcccagaac taccccagt gcatcaacat cgaggtcacg gcggcggct ccgacgcgcc        720 tgagggtact ctgggcgagg atctctacca tgacaccgac ccgggcattc tggtcgacat       780
ttacgagccc attgcgacgt ataccattcc ggggccgcct gagccgacgt tctag            835

<210> SEQ ID NO 10
<211> LENGTH: 253
<212> TYPE: PRT
<213> ORGANISM: Penicillium emersonii

<400> SEQUENCE: 10
```

| | | | | | | | | | | | | | | |
|---|---|---|---|---|---|---|---|---|---|---|---|---|---|---|
|Met|Leu|Ser|Ser|Thr|Thr|Arg|Thr|Leu|Ala|Phe|Thr|Gly|Leu|Ala|Gly|
|1| | | |5| | | | |10| | | | |15|

Leu Leu Ser Ala Pro Leu Val Lys Ala His Gly Phe Val Gln Gly Ile
                 20                   25                   30

Val Ile Gly Asp Gln Phe Tyr Ser Gly Tyr Ile Val Asn Ser Phe Pro
           35                 40                   45

Tyr Glu Ser Asn Pro Pro Val Ile Gly Trp Ala Thr Thr Ala Thr
 50               55               60

Asp Leu Gly Phe Val Asp Gly Thr Gly Tyr Gln Gly Pro Asp Ile Ile
65                70               75               80

Cys His Arg Asn Ala Thr Pro Ala Pro Leu Thr Ala Pro Val Ala Ala
                 85                   90               95

Gly Gly Thr Val Glu Leu Gln Trp Thr Pro Trp Pro Asp Ser His His
           100                105               110

Gly Pro Val Ile Thr Tyr Leu Ala Pro Cys Asn Gly Asn Cys Ser Thr
         115                120               125

Val Asp Lys Thr Thr Leu Glu Phe Phe Lys Ile Asp Gln Gln Gly Leu
   130                 135                140

Ile Asp Asp Thr Ser Pro Pro Gly Thr Trp Ala Ser Asp Asn Leu Ile
145               150               155             160

Ala Asn Asn Ser Trp Thr Val Thr Ile Pro Asn Ser Val Ala Pro
               165               170             175

Gly Asn Tyr Val Leu Arg His Glu Ile Ile Ala Leu His Ser Ala Asn
         180                185               190

Asn Lys Asp Gly Ala Gln Asn Tyr Pro Gln Cys Ile Asn Ile Glu Val
   195                 200               205

Thr Gly Gly Gly Ser Asp Ala Pro Glu Gly Thr Leu Gly Glu Asp Leu
   210                 215              220

Tyr His Asp Thr Asp Pro Gly Ile Leu Val Asp Ile Tyr Glu Pro Ile
225               230               235             240

Ala Thr Tyr Thr Ile Pro Gly Pro Pro Glu Pro Thr Phe
         245                250

<210> SEQ ID NO 11
<211> LENGTH: 1415
<212> TYPE: DNA
<213> ORGANISM: Aspergillus fumigatus

<400> SEQUENCE: 11

```
atggtccatc tatcttcatt ggcagcagcc ctggctgctc tgcctctgta tgtttaccca    60
ctcacgagag gaggaacagc tttgacattg ctatagtgta tatggagctg gcctgaacac   120
agcagccaaa gccaaaggac taaagtactt tggttccgcc acggacaatc cagagctcac   180
ggactctgcg tatgtcgcgc aactgagcaa caccgatgat tttggtcaaa tcacacccgg   240
aaactccatg aaggttttgc tacgtctgcc tccctggagc attgcctcaa agctaattg    300
gttgttttgt ttggatagtg ggatgccacc gagccttctc agaattcttt ttcgttcgca   360
aatggagacg ccgtggtcaa tctggcgaac aagaatggcc agctgatgcg atgccatact   420
ctggtctggc acagtcagct accgaactgg ggtatgtaaa cgtcttgtct attctcaaat   480
actctctaac agttgacagt ctctagcggg tcatggacca atgcgaccct tttggcggcc   540
atgaagaatc atatcaccaa tgtggttact cactacaagg ggaagtgcta cgcctgggat   600
gttgtcaatg aaggtttgtt gctccatcta tcctcaatag ttcttttgaa actgacaagc   660
ctgtcaatct agccctgaac gaggacggta ctttccgtaa ctctgtcttc taccagatca   720
```

```
tcggcccagc atacattcct attgcgttcg ccacggctgc tgccgcagat cccgacgtga      780
aactctacta caacgactac aacattgaat actcaggcgc caaagcgact gctgcgcaga      840
atatcgtcaa gatgatcaag gcctacggcg cgaagatcga cggcgtcggc ctccaggcac      900
actttatcgt cggcagcact ccgagtcaat cggatctgac daccgtcttg aagggctaca      960
ctgctctcgg cgttgaggtg gcctataccg aacttgacat ccgcatgcag ctgccctcga     1020
ccgccgcaaa gctggcccag cagtccactg acttccaagg cgtggccgca gcatgcgtta     1080
gcaccactgg ctgcgtgggt gtcactatct gggactggac cgacaagtac tcctgggtcc     1140
ccagcgtgtt ccaaggctac ggcgccccat tgccttggga tgagaactat gtgaagaagc     1200
cagcgtacga tggcctgatg gcgggtcttg agcaagcgg ctccggcacc acaacgacca     1260
ctactactac ttctactacg acaggaggta cggaccctac tggagtcgct cagaaatggg     1320
gacagtgtgg cggtattggc tggaccgggc caacaacttg tgtcagtggt accacttgcc     1380
aaaagctgaa tgactggtac tcacagtgcc tgtaa                                1415
```

<210> SEQ ID NO 12
<211> LENGTH: 397
<212> TYPE: PRT
<213> ORGANISM: Aspergillus fumigatus
<400> SEQUENCE: 12

```
Met Val His Leu Ser Ser Leu Ala Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
```

```
                   245                 250                 255
Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Cys Val Ser Thr
        275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Ser Thr
            340                 345                 350

Thr Thr Gly Gly Thr Asp Pro Thr Gly Val Ala Gln Lys Trp Gly Gln
        355                 360                 365

Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395

<210> SEQ ID NO 13
<211> LENGTH: 3060
<212> TYPE: DNA
<213> ORGANISM: Aspergillus fumigatus

<400> SEQUENCE: 13
atgagattcg gttggctcga ggtggccgct ctgacggccg cttctgtagc caatgcccag     60
gtttgtgatg ctttcccgtc attgtttcgg atatagttga caatagtcat ggaaataatc    120
aggaattggc tttctctcca ccattctacc cttcgccttg ggctgatggc cagggagagt    180
gggcagatgc ccatcgacgc gccgtcgaga tcgtttctca gatgacactg gcggagaagg    240
ttaaccttac aacgggtact gggtgggttg cgactttttt gttgacagtg agctttcttc    300
actgaccatc tacacagatg ggaaatggac cgatgcgtcg gtcaaaccgg cagcgttccc    360
aggtaagctt gcaattctgc aacaacgtgc aagtgtagtt gctaaaacgc ggtggtgcag    420
acttggtatc aactggggtc tttgtggcca ggattcccct tgggtatccc gtttctgtga    480
gctatacccg cggagtcttt cagtccttgt attatgtgct gatgattgtc tctgtatagc    540
tgacctcaac tccgccttcc ctgctggtac taatgtcgcc gcgacatggg acaagacact    600
cgcctacctt cgtggcaagg ccatgggtga ggaattcaac gacaagggcg tggacatttt    660 gctgggggcct gctgctggtc ctctcggcaa atacccggac ggcggcagaa tctgggaagg    720
cttctctcct gatccggttc tcactggtgt acttttcgcc gaaactatca agggtatcca    780
agacgcgggt gtgattgcta ctgccaagca ttacattctg aatgaacagg agcatttccg    840
acaggttggc gaggcccagg atatggttca acatcacg agacgatca gctccaacgt     900 ggatgacaag accatgcacg agttgtacct ttggtgagta gttgacactg caaatgagga    960
ccttgattga tttgactgac ctggaatgca ggcccctttgc agatgctgtg cgcggtaaga   1020
ttttccgtag acttgacctc gcgacgaaga atcgctgac gaaccatcgt agctggcgtt    1080
ggcgctgtca tgtgttccta caatcaaatc aacaacagct acggttgtca aacagtcaa    1140 actctcaaca agctcctcaa ggctgagctg ggcttccaag gcttcgtcat gagtgactgg    1200
agcgctcacc acagcggtgt cggcgctgcc ctcgctgggt tggatatgtc gatgcctgga    1260
```

-continued

```
gacatttcct tcgacgacgg actctccttc tggggcacga acctaactgt cagtgttctt    1320
aacggcaccg ttccagcctg cgtgtcgat gacatggctg ttcgtatcat gaccgcgtac    1380
tacaaggttg gtcgtgaccg tcttcgtatt ccccctaact tcagctcctg gacccgggat    1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga acacgggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctggggtagt ggtactgcca acttccctta ccttgtcacc    1740
cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataaccccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaacccct cctgaaggct ggcggcgctc ctggtggtaa ccctacccctt    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

<210> SEQ ID NO 14
<211> LENGTH: 863
<212> TYPE: PRT
<213> ORGANISM: Aspergillus fumigatus

<400> SEQUENCE: 14

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
        50                  55                  60

```
Gly Thr Gly Trp Glu Met Asp Arg Cys Val Gly Gln Thr Gly Ser Val
 65                  70                  75                  80

Pro Arg Leu Gly Ile Asn Trp Gly Leu Cys Gly Gln Asp Ser Pro Leu
             85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
            195                 200                 205

Tyr Gly Tyr Asn Ile Thr Glu Thr Ile Ser Ser Asn Val Asp Asp Lys
210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Ser Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His
        355                 360                 365

Ser Ala Val Ser Glu Gly Ala Trp Thr Lys Val Asn Asp Phe Val Asn
    370                 375                 380

Val Gln Arg Ser His Ser Gln Ile Ile Arg Glu Ile Gly Ala Ala Ser
385                 390                 395                 400

Thr Val Leu Leu Lys Asn Thr Gly Ala Leu Pro Leu Thr Gly Lys Glu
                405                 410                 415

Val Lys Val Gly Val Leu Gly Glu Asp Ala Gly Ser Asn Pro Trp Gly
            420                 425                 430

Ala Asn Gly Cys Pro Asp Arg Gly Cys Asp Asn Gly Thr Leu Ala Met
        435                 440                 445

Ala Trp Gly Ser Gly Thr Ala Asn Phe Pro Tyr Leu Val Thr Pro Glu
    450                 455                 460

Gln Ala Ile Gln Arg Glu Val Ile Ser Asn Gly Gly Asn Val Phe Ala
465                 470                 475                 480
```

Val Thr Asp Asn Gly Ala Leu Ser Gln Met Ala Asp Val Ala Ser Gln
            485                 490                 495

Ser Ser Val Ser Leu Val Phe Val Asn Ala Asp Ser Gly Glu Gly Phe
        500                 505                 510

Ile Ser Val Asp Gly Asn Glu Gly Asp Arg Lys Asn Leu Thr Leu Trp
        515                 520                 525

Lys Asn Gly Glu Ala Val Ile Asp Thr Val Val Ser His Cys Asn Asn
    530                 535                 540

Thr Ile Val Val Ile His Ser Val Gly Pro Val Leu Ile Asp Arg Trp
545                 550                 555                 560

Tyr Asp Asn Pro Asn Val Thr Ala Ile Ile Trp Ala Gly Leu Pro Gly
                565                 570                 575

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Asn Gly Asn Gly Ala Pro Gln
        610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
        690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
        770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
850                 855                 860

<210> SEQ ID NO 15
<211> LENGTH: 2376
<212> TYPE: DNA
<213> ORGANISM: Aspergillus fumigatus

<400> SEQUENCE: 15

```
atggcggttg ccaaatctat tgctgccgtg ctggtagcac tgttgcctgg tgcgcttgct    60
caggcgaata caagctatgt tgattacaat gtggaggcga atccggatct caccccctcag   120
tcggtcgcta cgattgacct gtcctttccc gactgcgaga atggaccgct cagcaagact   180
ctcgtttgcg acacgtcggc tcggccgcat gaccgagctg ctgccctggt tccatgttc    240
accttcgagg agctggtgaa caacacaggc aacactagcc ctggtgttcc aagacttggt   300
ctccctccgt accaagtatg gagcgaggct ctccatggac ttgaccgcgc caacttcaca   360
aacgagggag agtacagctg ggccacctcg ttccccatgc ctatcctgac aatgtcggcc   420
ttgaaccgaa ccctgatcaa ccagatcgcg accatcatcg caactcaagg acgagctttc   480
aataacgttg ggcggtatgg gctggacgtg tacgccccga atataaatgc attcagatcg   540
gctatgtggg gaagaggtca agagaccccc ggagaagacg cttactgcct ggcatcggcg   600
tatgcgtacg agtatatcac tggcatccag ggtggtgttg atccggaaca cctcaagttg   660
gtggccactg ccaaacacta tgcgggctac gatcttgaga ctgggacgg tcactcccgt   720
ttgggcaacg atatgaacat tacacagcag gaactttccg aatactacac ccctcagttc   780
cttgttgcag ccagagacgc caaagtgcac agtgtcatgt gctcctacaa cgcggtaaat   840
ggggtgccca gctgcgcaaa ctcgttcttc ctccagaccc tcctccgtga cacattcggc   900
ttcgtcgagg atggttatgt atccagcgac tgcgactcgg cgtacaatgt ctggaacccg   960
cacgagtttg cggccaacat cacgggggcc gctgcagact ctatccgggc ggggacggac  1020
attgattgcg gcactactta tcaatactat ttcggcgaag cctttgacga gcaagaggtc  1080
acccgtgcag aaatcgaaag aggtgtgatc cgcctgtaca gcaacttggt gcgtctcggc  1140
tatttcgatg gcaatggaag cgtgtatcgg gacctgacgt ggaatgatgt cgtgaccacg  1200
gatgcctgga atatctcata cgaagccgct gtagaaggca ttgtcctact gaagaacgat  1260
ggaaccttgc ctctcgccaa gtcggtccgc agtgttgcat tgattgggcc ctggatgaat  1320
gtgacgactc agcttcaggg caactacttt ggaccggcgc cttatctgat tagtccgttg  1380
aatgccttcc agaattctga cttcgacgtg aactacgctt tcggcacgaa catttcatcc  1440
cactccacag atgggttttc cgaggcgttg tctgctgcga agaaatccga cgtcatcata  1500
ttcgcgggcg ggattgacaa cactttggaa gcagaagcca tggatcgcat gaatatcaca  1560
tggcccggca atcagctaca gctcatcgac cagttgagcc aactcggcaa accgctgatc  1620
gtcctccaga tgggcggcgg ccaagtcgac tcctcctcgc tcaagtccaa caagaatgtc  1680
aactcctga tctggggtgg ataccccgga caatccggcg gcaggctct cctagacatc    1740
atcaccggca agcgcgcccc cgccggccga ctcgtggtca cgcagtaccc ggccgaatac   1800
gcaacccagt tccccgccac cgacatgagc ctgcggcctc acggcaataa tcccggccag   1860
acctacatgt ggtacaccgg caccccgtc tacgagtttg ccacgggct cttctacacg    1920
accttccacg cctccctccc tggcaccggc aaggacaaga cctccttcaa catccaagac  1980
ctcctcacgc agccgcatcc gggcttcgca aacgtcgagc aaatgccttt gctcaacttc  2040
accgtgacga tcaccaatac cggcaaggtc gcttccgact acactgctat gctcttcgcg  2100
aacaccaccg cgggacctgc tccataccog aacaagtggc tcgtcggctt cgaccggctg  2160
gcgagcctgg aaccgcacag gtcgcagact atgaccatcc ccgtgactat cgacagcgtg  2220
gctcgtacgg atgaggccgg caatcgggtt ctctacccgg gaaagtacga gttggccctg  2280
aacaatgagc ggtcggttgt ccttcagttt gtgctgacag gccgagaggc tgtgattttc  2340
```
aagtggcctg tagagcagca gcagatttcg tctgcg                                    2376

<210> SEQ ID NO 16
<211> LENGTH: 792
<212> TYPE: PRT
<213> ORGANISM: Aspergillus fumigatus

<400> SEQUENCE: 16

Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
                20                  25                  30

Ala Asn Pro Asp Leu Thr Pro Gln Ser Val Ala Thr Ile Asp Leu Ser
            35                  40                  45

Phe Pro Asp Cys Glu Asn Gly Pro Leu Ser Lys Thr Leu Val Cys Asp
        50                  55                  60

Thr Ser Ala Arg Pro His Asp Arg Ala Ala Leu Val Ser Met Phe
65                  70                  75                  80

Thr Phe Glu Glu Leu Val Asn Asn Thr Gly Asn Thr Ser Pro Gly Val
                85                  90                  95

Pro Arg Leu Gly Leu Pro Pro Tyr Gln Val Trp Ser Glu Ala Leu His
            100                 105                 110

Gly Leu Asp Arg Ala Asn Phe Thr Asn Glu Gly Glu Tyr Ser Trp Ala
        115                 120                 125

Thr Ser Phe Pro Met Pro Ile Leu Thr Met Ser Ala Leu Asn Arg Thr
130                 135                 140

Leu Ile Asn Gln Ile Ala Thr Ile Ile Ala Thr Gln Gly Arg Ala Phe
145                 150                 155                 160

Asn Asn Val Gly Arg Tyr Gly Leu Asp Val Tyr Ala Pro Asn Ile Asn
                165                 170                 175

Ala Phe Arg Ser Ala Met Trp Gly Arg Gly Gln Glu Thr Pro Gly Glu
            180                 185                 190

Asp Ala Tyr Cys Leu Ala Ser Ala Tyr Ala Tyr Glu Tyr Ile Thr Gly
        195                 200                 205

Ile Gln Gly Gly Val Asp Pro Glu His Leu Lys Leu Val Ala Thr Ala
210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                245                 250                 255

Thr Pro Gln Phe Leu Val Ala Ala Arg Asp Ala Lys Val His Ser Val
            260                 265                 270

Met Cys Ser Tyr Asn Ala Val Asn Gly Val Pro Ser Cys Ala Asn Ser
        275                 280                 285

Phe Phe Leu Gln Thr Leu Leu Arg Asp Thr Phe Gly Phe Val Glu Asp
    290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Asp Ser Ile Arg
                325                 330                 335

Ala Gly Thr Asp Ile Asp Cys Gly Thr Thr Tyr Gln Tyr Tyr Phe Gly
            340                 345                 350

Glu Ala Phe Asp Glu Gln Glu Val Thr Arg Ala Glu Ile Glu Arg Gly
        355                 360                 365

Val Ile Arg Leu Tyr Ser Asn Leu Val Arg Leu Gly Tyr Phe Asp Gly
    370             375             380

Asn Gly Ser Val Tyr Arg Asp Leu Thr Trp Asn Asp Val Val Thr Thr
385             390             395             400

Asp Ala Trp Asn Ile Ser Tyr Glu Ala Ala Val Glu Gly Ile Val Leu
            405             410             415

Leu Lys Asn Asp Gly Thr Leu Pro Leu Ala Lys Ser Val Arg Ser Val
            420             425             430

Ala Leu Ile Gly Pro Trp Met Asn Val Thr Thr Gln Leu Gln Gly Asn
        435             440             445

Tyr Phe Gly Pro Ala Pro Tyr Leu Ile Ser Pro Leu Asn Ala Phe Gln
    450             455             460

Asn Ser Asp Phe Asp Val Asn Tyr Ala Phe Gly Thr Asn Ile Ser Ser
465             470             475             480

His Ser Thr Asp Gly Phe Ser Glu Ala Leu Ser Ala Ala Lys Lys Ser
                485             490             495

Asp Val Ile Ile Phe Ala Gly Gly Ile Asp Asn Thr Leu Glu Ala Glu
            500             505             510

Ala Met Asp Arg Met Asn Ile Thr Trp Pro Gly Asn Gln Leu Gln Leu
        515             520             525

Ile Asp Gln Leu Ser Gln Leu Gly Lys Pro Leu Ile Val Leu Gln Met
    530             535             540

Gly Gly Gly Gln Val Asp Ser Ser Ser Leu Lys Ser Asn Lys Asn Val
545             550             555             560

Asn Ser Leu Ile Trp Gly Gly Tyr Pro Gly Gln Ser Gly Gly Gln Ala
            565             570             575

Leu Leu Asp Ile Ile Thr Gly Lys Arg Ala Pro Ala Gly Arg Leu Val
            580             585             590

Val Thr Gln Tyr Pro Ala Glu Tyr Ala Thr Gln Phe Pro Ala Thr Asp
    595             600             605

Met Ser Leu Arg Pro His Gly Asn Asn Pro Gly Gln Thr Tyr Met Trp
    610             615             620

Tyr Thr Gly Thr Pro Val Tyr Glu Phe Gly His Gly Leu Phe Tyr Thr
625             630             635             640

Thr Phe His Ala Ser Leu Pro Gly Thr Gly Lys Asp Lys Thr Ser Phe
            645             650             655

Asn Ile Gln Asp Leu Leu Thr Gln Pro His Pro Gly Phe Ala Asn Val
            660             665             670

Glu Gln Met Pro Leu Leu Asn Phe Thr Val Thr Ile Thr Asn Thr Gly
        675             680             685

Lys Val Ala Ser Asp Tyr Thr Ala Met Leu Phe Ala Asn Thr Thr Ala
    690             695             700

Gly Pro Ala Pro Tyr Pro Asn Lys Trp Leu Val Gly Phe Asp Arg Leu
705             710             715             720

Ala Ser Leu Glu Pro His Arg Ser Gln Thr Met Thr Ile Pro Val Thr
            725             730             735

Ile Asp Ser Val Ala Arg Thr Asp Glu Ala Gly Asn Arg Val Leu Tyr
            740             745             750

Pro Gly Lys Tyr Glu Leu Ala Leu Asn Asn Glu Arg Ser Val Val Leu
        755             760             765

Gln Phe Val Leu Thr Gly Arg Glu Ala Val Ile Phe Lys Trp Pro Val
    770             775             780

Glu Gln Gln Gln Ile Ser Ser Ala

<210> SEQ ID NO 17
<211> LENGTH: 1849
<212> TYPE: DNA
<213> ORGANISM: Trichoderma reesei

<400> SEQUENCE: 17

| | | | | | |
|---|---|---|---|---|---|
| tgccatttct | gacctggata | ggttttccta | tggtcattcc | tataagagac | acgctctttc | 60 |
| gtcggcccgt | agatatcaga | ttggtattca | gtcgcacaga | cgaaggtgag | ttgatcctcc | 120 |
| aacatgagtt | ctatgagccc | ccccttgcc | cccccgtt | caccttgacc | tgcaatgaga | 180 |
| atcccacctt | ttacaagagc | atcaagaagt | attaatggcg | ctgaatagcc | tctgctcgat | 240 |
| aatatctccc | cgtcatcgac | aatgaacaag | tccgtggctc | cattgctgct | tgcagcgtcc | 300 |
| atactatatg | gcggcgccgt | cgcacagcag | actgtctggg | gccagtgtgg | aggtattggt | 360 |
| tggagcggac | ctacgaattg | tgctcctggc | tcagcttgtt | cgaccctcaa | tccttattat | 420 |
| gcgcaatgta | ttccgggagc | cactactatc | accacttcga | cccggccacc | atccggtcca | 480 |
| accaccacca | ccagggctac | ctcaacaagc | tcatcaactc | cacccacgag | ctctggggtc | 540 |
| cgatttgccg | gcgttaacat | cgcgggtttt | gactttggct | gtaccacaga | gtgagtaccc | 600 |
| ttgtttcctg | gtgttgctgg | ctggttgggc | gggtatacag | cgaagcggac | gcaagaacac | 660 |
| cgccggtccg | ccaccatcaa | gatgtgggtg | gtaagcggcg | gtgtttgta | caactacctg | 720 |
| acagctcact | caggaaatga | gaattaatgg | aagtcttgtt | acagtggcac | ttgcgttacc | 780 |
| tcgaaggttt | atcctccgtt | gaagaacttc | accggctcaa | acaactaccc | cgatggcatc | 840 |
| ggccagatgc | agcacttcgt | caacgaggac | gggatgacta | ttttccgctt | acctgtcgga | 900 |
| tggcagtacc | tcgtcaacaa | caatttgggc | ggcaatcttg | attccacgag | catttccaag | 960 |
| tatgatcagc | ttgttcaggg | gtgcctgtct | ctgggcgcat | actgcatcgt | cgacatccac | 1020 |
| aattatgctc | gatggaacgg | tgggatcatt | ggtcagggcg | gccctactaa | tgctcaattc | 1080 |
| acgagccttt | ggtcgcagtt | ggcatcaaag | tacgcatctc | agtcgagggt | gtggttcggc | 1140 |
| atcatgaatg | agccccacga | cgtgaacatc | aacacctggg | ctgccacggt | ccaagaggtt | 1200 |
| gtaaccgcaa | tccgcaacgc | tggtgctacg | tcgcaattca | tctctttgcc | tggaaatgat | 1260 |
| tggcaatctg | ctggggcttt | catatccgat | ggcagtgcag | ccgccctgtc | tcaagtcacg | 1320 |
| aacccggatg | ggtcaacaac | gaatctgatt | tttgacgtgc | acaaatactt | ggactcagac | 1380 |
| aactccggta | ctcacgccga | atgtactaca | aataacattg | acggcgcctt | ttctccgctt | 1440 |
| gccacttggc | tccgacagaa | caatcgccag | gctatcctga | cagaaaccgg | tggtggcaac | 1500 |
| gttcagtcct | gcatacaaga | catgtgccag | caaatccaat | atctcaacca | gaactcagat | 1560 |
| gtctatcttg | gctatgttgg | ttggggtgcc | ggatcatttg | atagcacgta | tgtcctgacg | 1620 |
| gaaacaccga | ctggcagtgg | taactcatgg | acggacacat | ccttggtcag | ctcgtgtctc | 1680 |
| gcaagaaagt | agcactctga | gctgaatgca | gaagcctcgc | caacgtttgt | atctcgctat | 1740 |
| caaacatagt | agctactcta | tgaggctgtc | tgttctcgat | ttcagcttta | tatagtttca | 1800 |
| tcaaacagta | catattccct | ctgtggccac | gcaaaaaaaa | aaaaaaaaa | | 1849 |

<210> SEQ ID NO 18
<211> LENGTH: 418
<212> TYPE: PRT
<213> ORGANISM: Trichoderma reesei

<400> SEQUENCE: 18

```
Met Asn Lys Ser Val Ala Pro Leu Leu Leu Ala Ala Ser Ile Leu Tyr
1               5                   10                  15

Gly Gly Ala Val Ala Gln Gln Thr Val Trp Gly Gln Cys Gly Gly Ile
            20                  25                  30

Gly Trp Ser Gly Pro Thr Asn Cys Ala Pro Gly Ser Ala Cys Ser Thr
        35                  40                  45

Leu Asn Pro Tyr Tyr Ala Gln Cys Ile Pro Gly Ala Thr Thr Ile Thr
    50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
            115                 120                 125

Asn Asn Tyr Pro Asp Gly Ile Gly Gln Met Gln His Phe Val Asn Glu
    130                 135                 140

Asp Gly Met Thr Ile Phe Arg Leu Pro Val Gly Trp Gln Tyr Leu Val
145                 150                 155                 160

Asn Asn Asn Leu Gly Gly Asn Leu Asp Ser Thr Ser Ile Ser Lys Tyr
                165                 170                 175

Asp Gln Leu Val Gln Gly Cys Leu Ser Leu Gly Ala Tyr Cys Ile Val
            180                 185                 190

Asp Ile His Asn Tyr Ala Arg Trp Asn Gly Gly Ile Ile Gly Gln Gly
    195                 200                 205

Gly Pro Thr Asn Ala Gln Phe Thr Ser Leu Trp Ser Gln Leu Ala Ser
        210                 215                 220

Lys Tyr Ala Ser Gln Ser Arg Val Trp Phe Gly Ile Met Asn Glu Pro
225                 230                 235                 240

His Asp Val Asn Ile Asn Thr Trp Ala Ala Thr Val Gln Glu Val Val
                245                 250                 255

Thr Ala Ile Arg Asn Ala Gly Ala Thr Ser Gln Phe Ile Ser Leu Pro
            260                 265                 270

Gly Asn Asp Trp Gln Ser Ala Gly Ala Phe Ile Ser Asp Gly Ser Ala
    275                 280                 285

Ala Ala Leu Ser Gln Val Thr Asn Pro Asp Gly Ser Thr Thr Asn Leu
        290                 295                 300

Ile Phe Asp Val His Lys Tyr Leu Asp Ser Asp Asn Ser Gly Thr His
305                 310                 315                 320

Ala Glu Cys Thr Thr Asn Asn Ile Asp Gly Ala Phe Ser Pro Leu Ala
                325                 330                 335

Thr Trp Leu Arg Gln Asn Asn Arg Gln Ala Ile Leu Thr Glu Thr Gly
            340                 345                 350

Gly Gly Asn Val Gln Ser Cys Ile Gln Asp Met Cys Gln Gln Ile Gln
    355                 360                 365

Tyr Leu Asn Gln Asn Ser Asp Val Tyr Leu Gly Tyr Val Gly Trp Gly
        370                 375                 380

Ala Gly Ser Phe Asp Ser Thr Tyr Val Leu Thr Glu Thr Pro Thr Gly
385                 390                 395                 400
```

```
Ser Gly Asn Ser Trp Thr Asp Thr Ser Leu Val Ser Ser Cys Leu Ala
            405                 410                 415
Arg Lys
```